United States Patent
Burkhart et al.

(10) Patent No.: US 10,646,566 B2
(45) Date of Patent: May 12, 2020

(54) COMPOSITIONS AND USES

(71) Applicant: GLAXOSMITHKLINE BIOLOGICALS, SA, Rixensart (BE)

(72) Inventors: David Burkhart, Research Triangle Park, NC (US); Michael Cochran, Research Triangle Park, NC (US); Christopher W Cluff, Research Triangle Park, NC (US); Daniel Larocque, Research Triangle Park, NC (US); Helene G Bazin-Lee, Research Triangle Park, NC (US); Julien St Jean, Research Triangle Park, NC (US)

(73) Assignee: GLAXOSMITHKLINE BIOLOGICALS S.A., Rixensart (BE)

( * ) Notice: Subject to any disclaimer, the term of this patent is extended or adjusted under 35 U.S.C. 154(b) by 0 days.

(21) Appl. No.: 15/556,520

(22) PCT Filed: Mar. 9, 2016

(86) PCT No.: PCT/IB2016/051336
§ 371 (c)(1),
(2) Date: Sep. 7, 2017

(87) PCT Pub. No.: WO2016/142880
PCT Pub. Date: Sep. 15, 2016

(65) Prior Publication Data
US 2018/0036403 A1      Feb. 8, 2018

Related U.S. Application Data

(60) Provisional application No. 62/130,812, filed on Mar. 10, 2015.

(51) Int. Cl.
| | | |
|---|---|---|
| A61K 39/39 | (2006.01) | |
| A61K 31/522 | (2006.01) | |
| A61K 31/52 | (2006.01) | |
| A61K 39/00 | (2006.01) | |

(52) U.S. Cl.
CPC .............. *A61K 39/39* (2013.01); *A61K 31/52* (2013.01); *A61K 31/522* (2013.01); *A61K 2039/555* (2013.01); *A61K 2039/55511* (2013.01); *A61K 2039/627* (2013.01)

(58) Field of Classification Search
CPC ........................................... A61K 39/39
See application file for complete search history.

(56) References Cited

FOREIGN PATENT DOCUMENTS

| WO | 2010018134 A1 | 2/2010 | |
|---|---|---|---|
| WO | 2011017611 A1 | 2/2011 | |
| WO | WO2011017611 | * 2/2011 | ............. A01N 43/90 |
| WO | WO 2016/075661 A1 | 5/2016 | |

OTHER PUBLICATIONS

Written Opinion of the International Searching Authority in PCT/IB2016/051336.
International Search Report in PCT/IB2016/051336.
Michael Chan et al. Synthesis and immunological characterization of toll-like receptor 7 agonistic conjugates, Bioconjugate Chemistry, ACS, Washington, DC, US, vol. 20, No. 6, Jun. 17, 2009 (Jun. 17, 2009), pp. 1194-1200.
Keith Biggadike et al: Discovery of 6-Amino-2-{[(1 S)-1-methylbutyl]oxy}-9-[5-(I piperidinyl)pentyl]-7,9-dihydro-8H-purin-8-one (GSK2245035), a Highly Potent and Selective Intranasal Toll-Like Receptor 7 Agonist for the Treatment of Asthma, Journal of Medicinal Chemistry, vol. 59, No. 5, Mar. 10, 2016 (Mar. 10, 2016), pp. 1711-1726.
Peter H. Goff et al: Synthetic Toll-Like Receptor 4 (TLR4) and TLR7 Ligands as Influenza Virus Vaccine Adjuvants Induce Rapid, Sustained, and Broadly Protective Responses, Journal of Virology, vol. 89, No. 6, Jan. 7, 2015 (Jan. 7, 2015), pp. 3221-3235.
Bazin, et al. "Structural requirements for TLR7-selective signaling by 9-(4-piperidinylalkyl)-8-oxoadenine derivatives" Bioorganic & Medicinal Chemstry Letters, vol. 25, 2015, pp. 1318-1323.

* cited by examiner

*Primary Examiner* — Paul V Ward
(74) *Attorney, Agent, or Firm* — Birch, Stewart, Kolasch & Birch, LLP

(57) ABSTRACT

The present invention relates to immunogenic compositions and methods for producing them, and in particular, immunogenic compositions comprising a protein antigen cross linked to an oxoadenine adjuvant.

16 Claims, 19 Drawing Sheets

Specification includes a Sequence Listing.

General process flow diagram

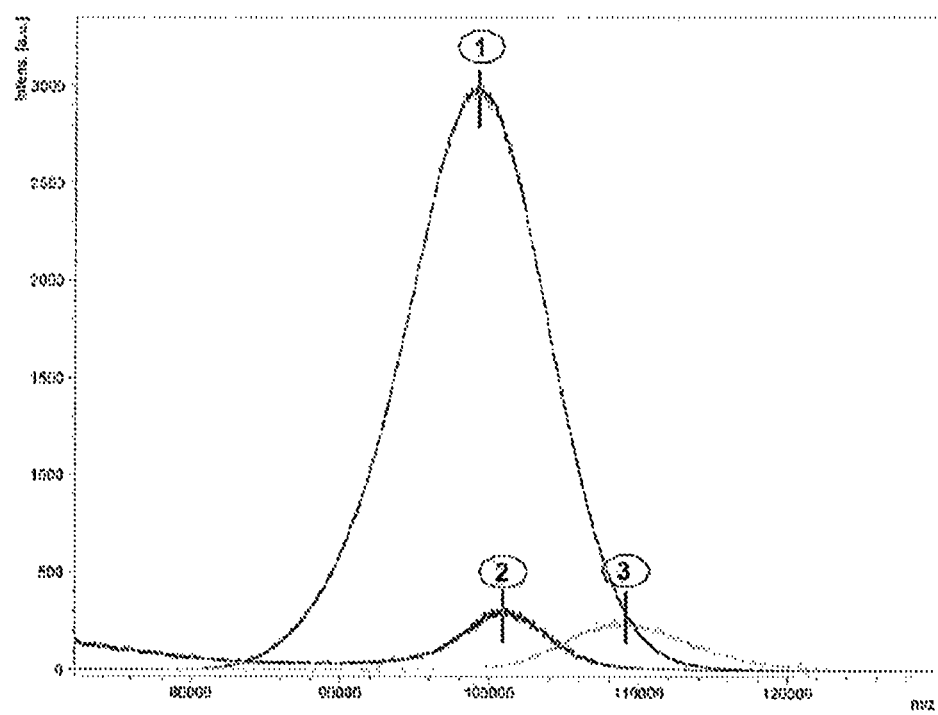
Figure 2. MALDI-TOF MS of an antigen (1), the antigen conjugated to GMBS (2) and the antigen conjugated to an adjuvant (3). The shifts in molecular weight indicate an average of 11 copies of GMBS per antigen and an average of 3 copies of adjuvant per antigen.

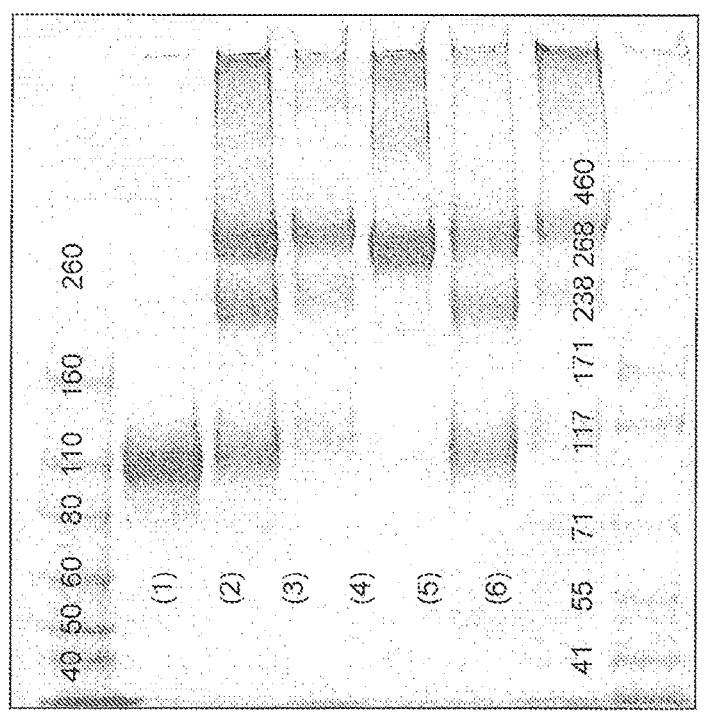

Figure 3. SDS-PAGE of an antigen and antigen/adjuvant conjugates using a 3-8% tris-acetate gel. Antigen (1), antigen conjugated to a TLR-7/8 agonist (2), antigen conjugated to a TLR-2 agonist (3), antigen crosslinked with GMBS with no adjuvant (4), antigen conjugated to a TLR- 7/8 agonist (5), antigen conjugated to both TLR-7/8 and TLR-2 agonists (6).The increase in molecular weight of the conjugates is shown by the shift up of the bands in the gel with respect to the unconjugated antigen. The gel also shows the dimer and trimer are stabilized by the conjugation procedure.

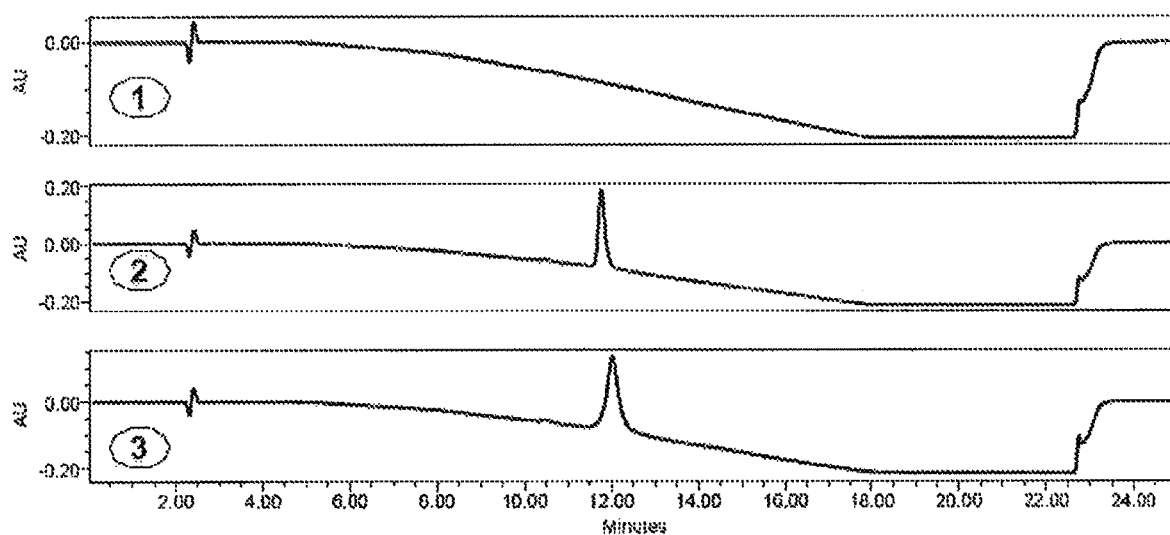
Figure 4 The RP-HPLC chromatogram of buffer only (1), antigen only (2) and antigen/adjuvant conjugate (3) shows a small shift in retention time for the conjugate and no unconjugated adjuvant.

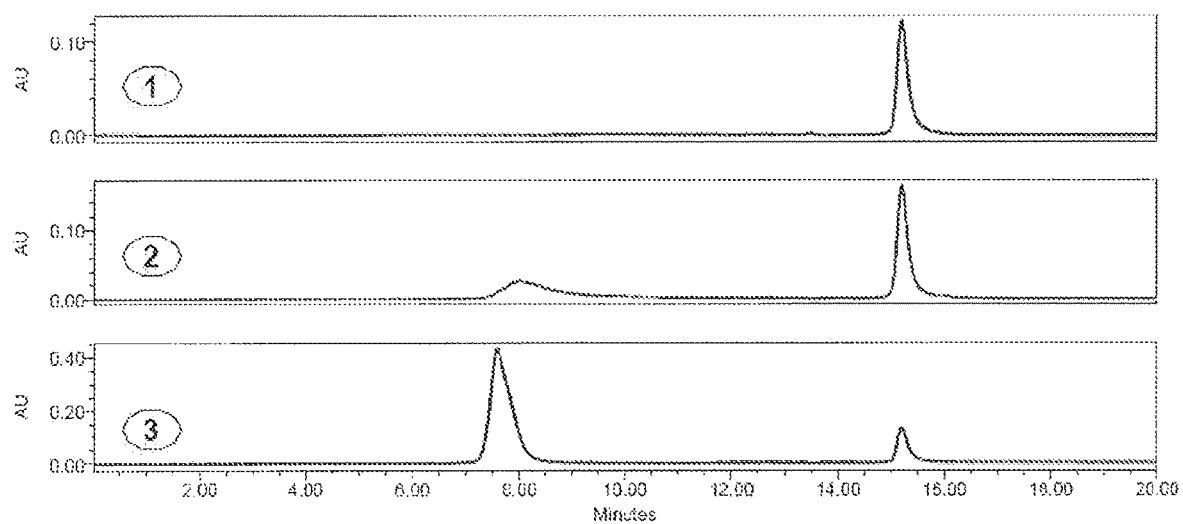
Figure 5. The SEC-HPLC chromatogram of buffer only (1), antigen only (2) and antigen/adjuvant conjugate (3) shows a shift in retention time for the conjugate and no unconjugated adjuvant.

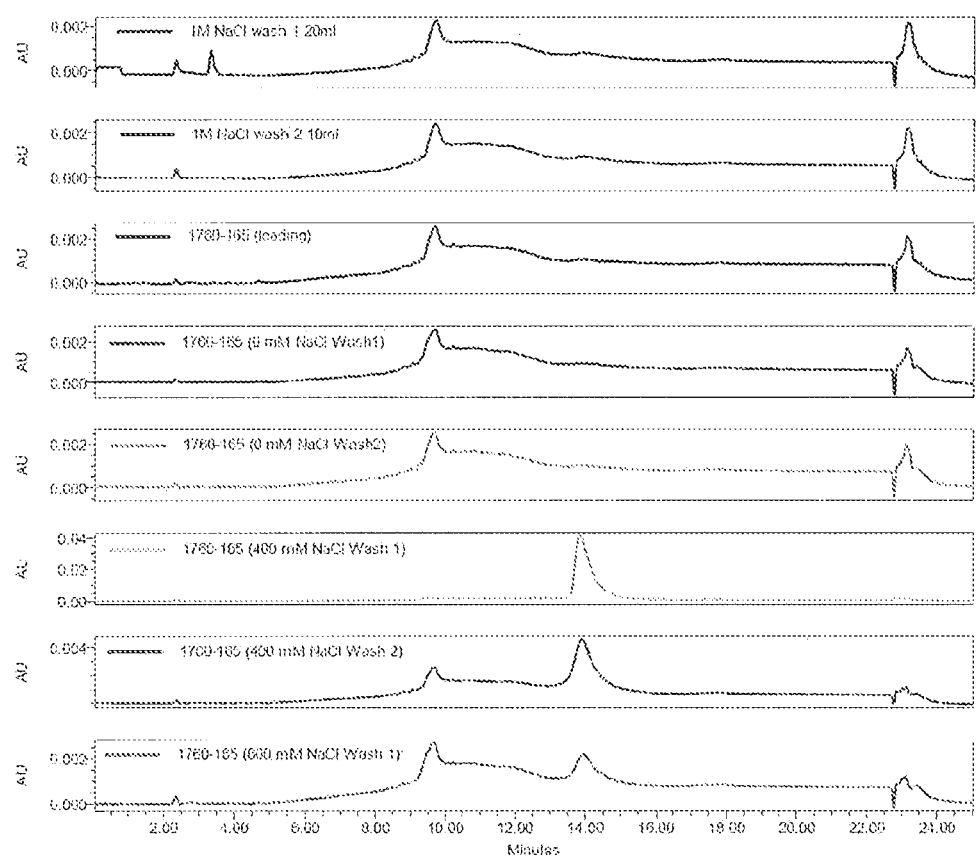
FIGURE 6 data showing RP-HPLC of fractions collected during ion exchange chromatography of a CRM-Compound B conjugate

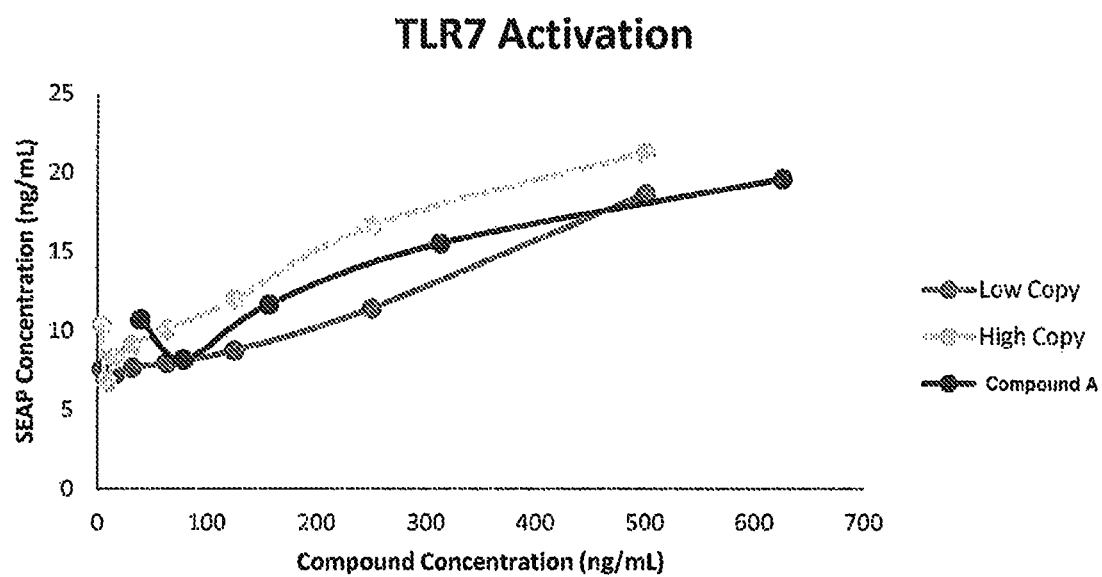
Figure 7: TLR7 activation at very low doses by CRM-Compound A Lower Copy and CRM-Compound A Higher Copy using the TLR7/NF-κB/SEAP Stable Reporter Cell Line (Imgenex corp). CRM-Compound A conjugates (Lower Copy or Higher Copy number) do activate human TLR7 pathway as efficiently as Compound A alone.

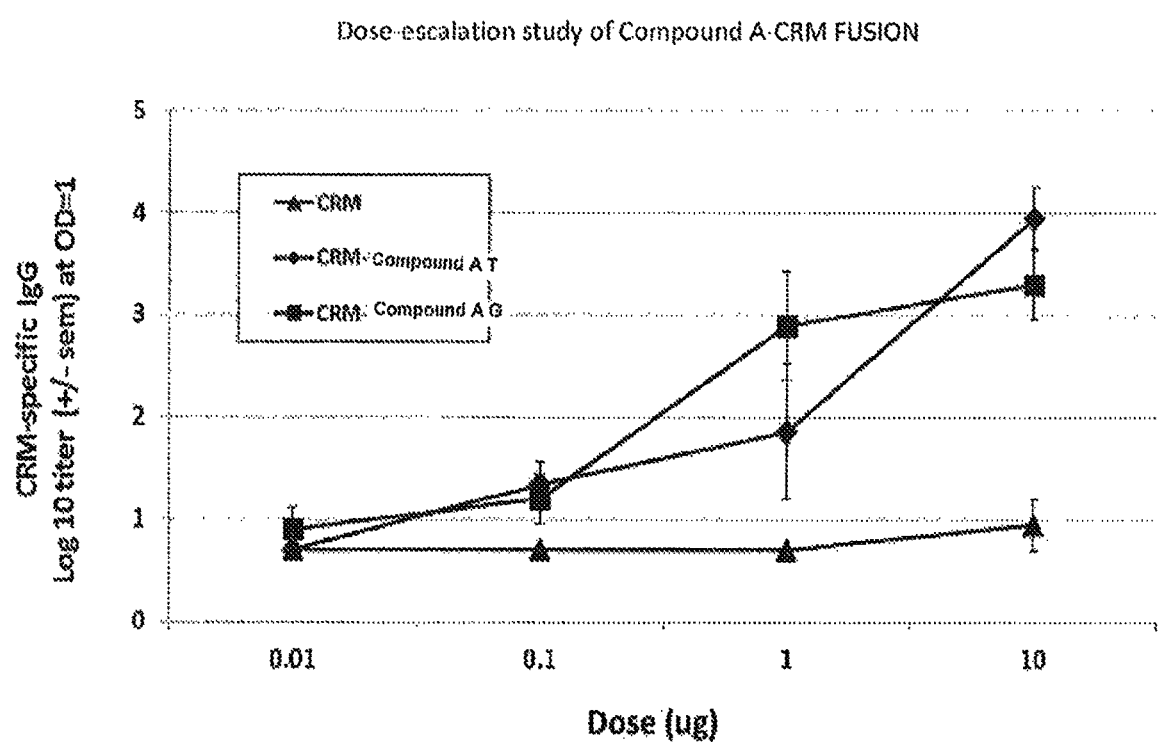
Figure 8: Dose-escalation study of CRM-Compound A showing that a dose-response in term of CRM-specific IgG is observed from CRM-Compound A conjugates in 2 different configurations in BALB/c mice using T vs G configuration.

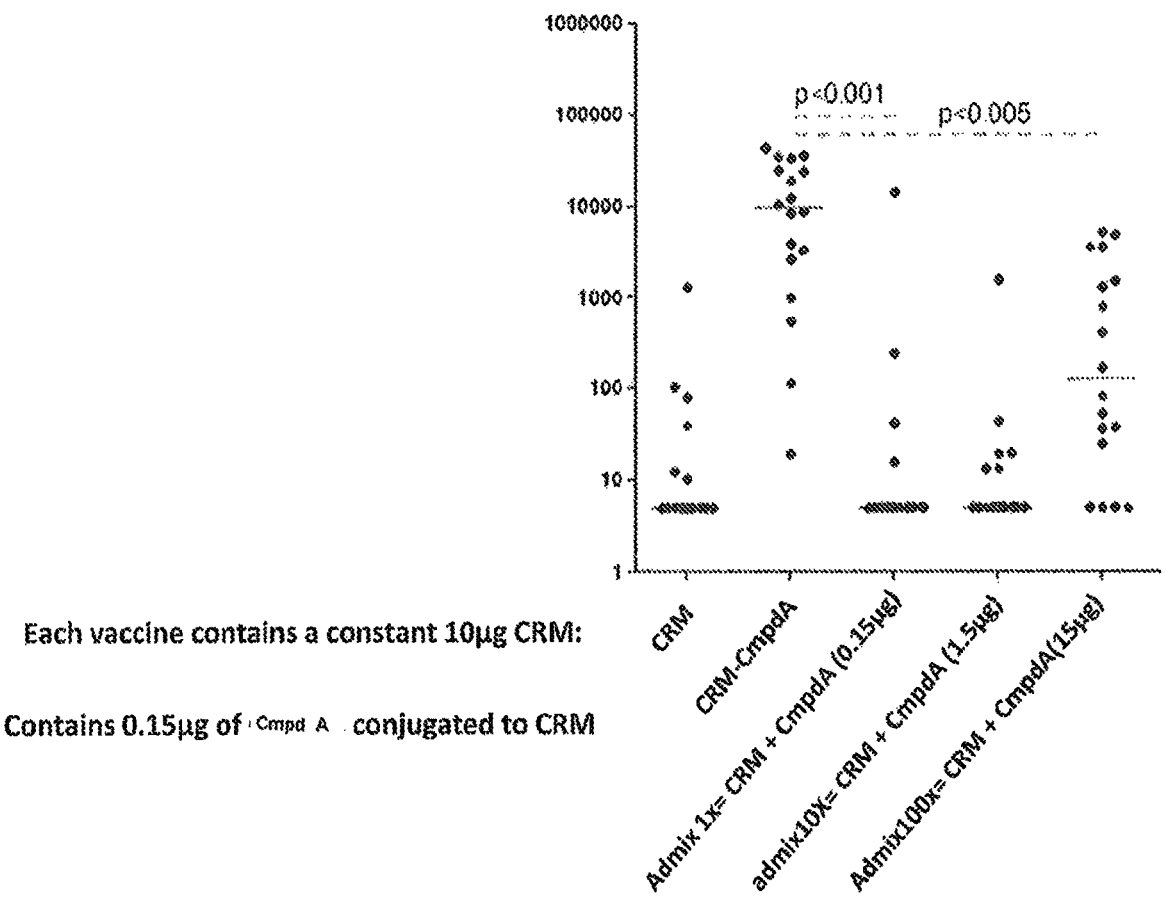
Figure 9: Proof-of-concept study in mice showing that CRM-Compound A antigen-adjuvant conjugates (Fusion) induce a significant humoral response based on CRM197 specific antibody level. Anti CRM specific IgG titers-serum day 49 (7 days post 3)

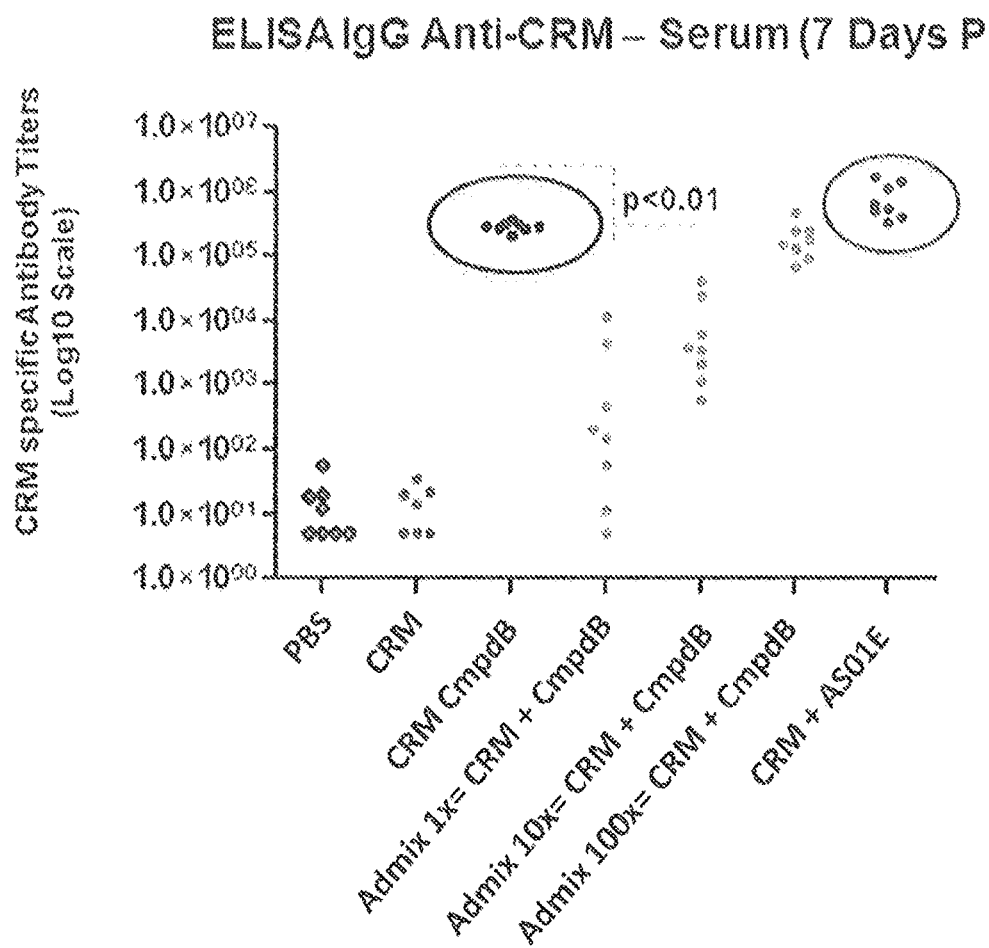
Figure 10a: Proof-of-concept study in mice showing that CRM-Compound B fused conjugates (FUSION) are more efficient even with 10X less of adjuvant to mount a significant humoral response based on CRM197 specific antibody.

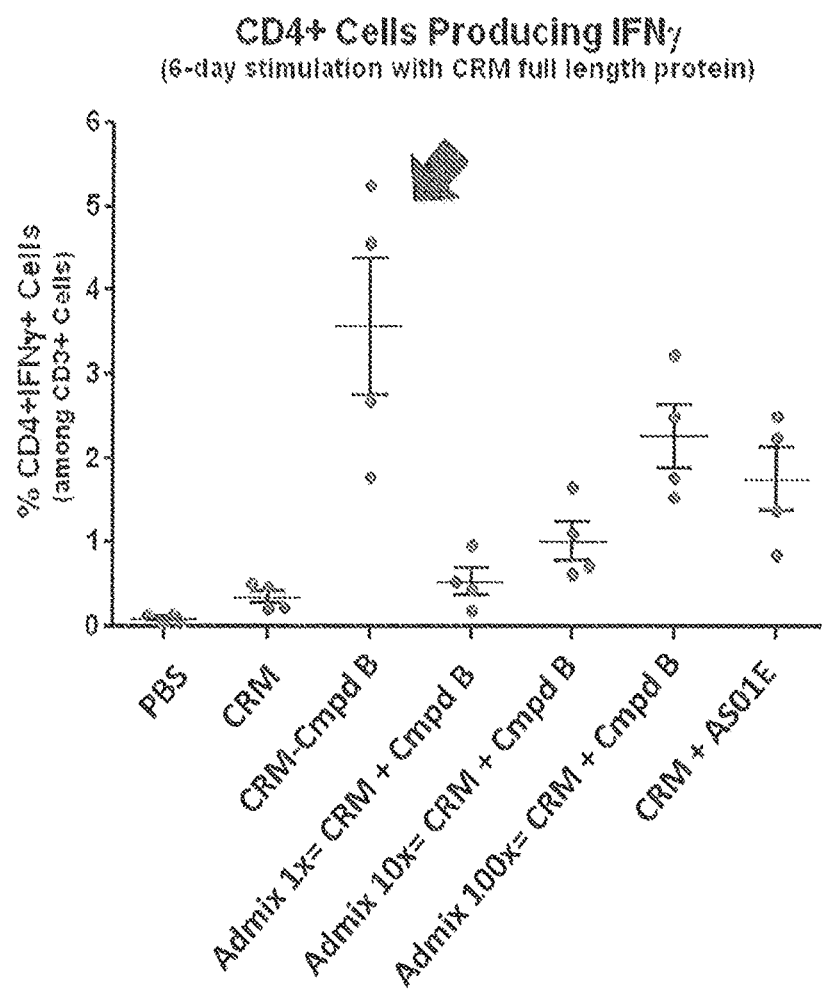
Figure 10b: T cell activation assessment from splenocytes coming from immunized mice shows that the CRM-Compound B fused conjugate trigger an higher CRM197 specifics T cell activation compared to CRM + Compound B Admix at 1X or 10X concentration.

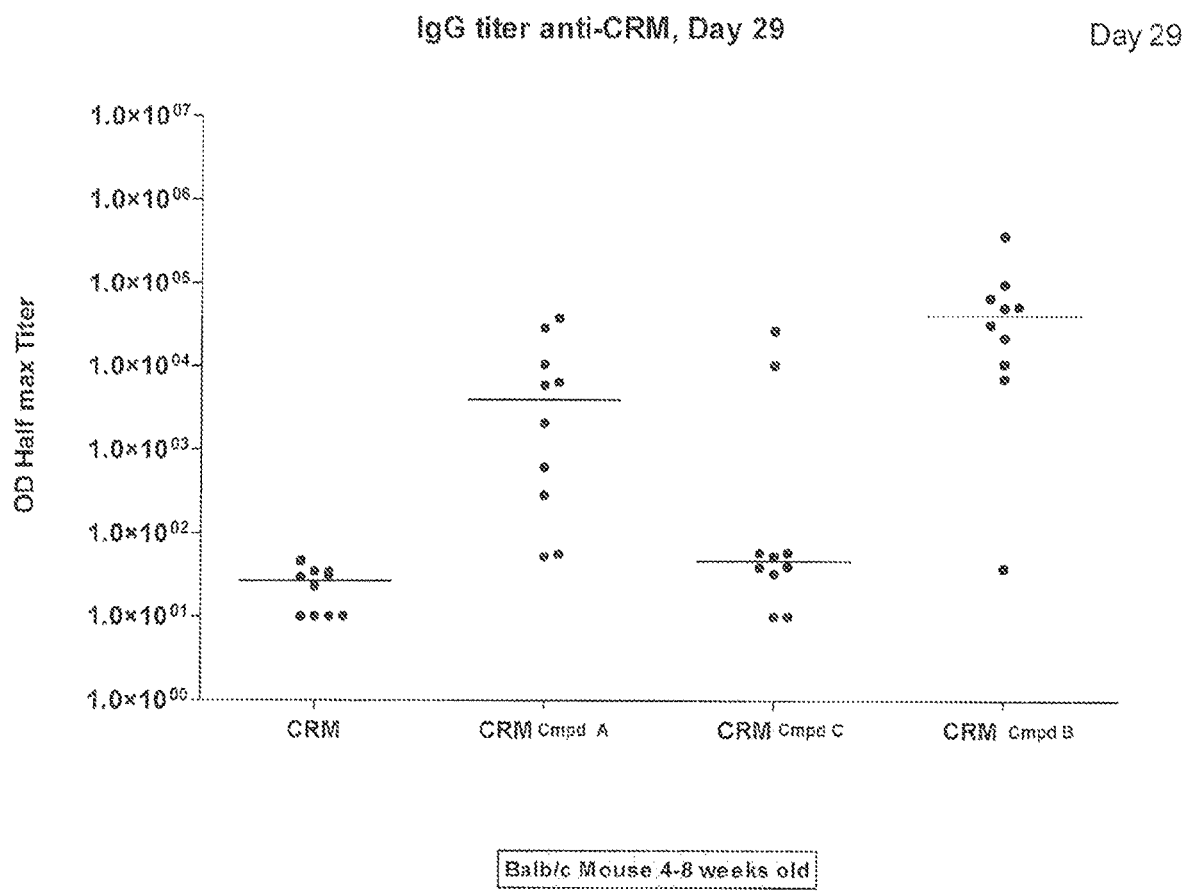
Figure 11a: CRM-specific antibody level at 7 days post 2$^{nd}$ injection Immunogenicity shows that CRM-Compound B conjugate is more immunogenic than CRM-Compound A and CRM-Compound C constructs in mice

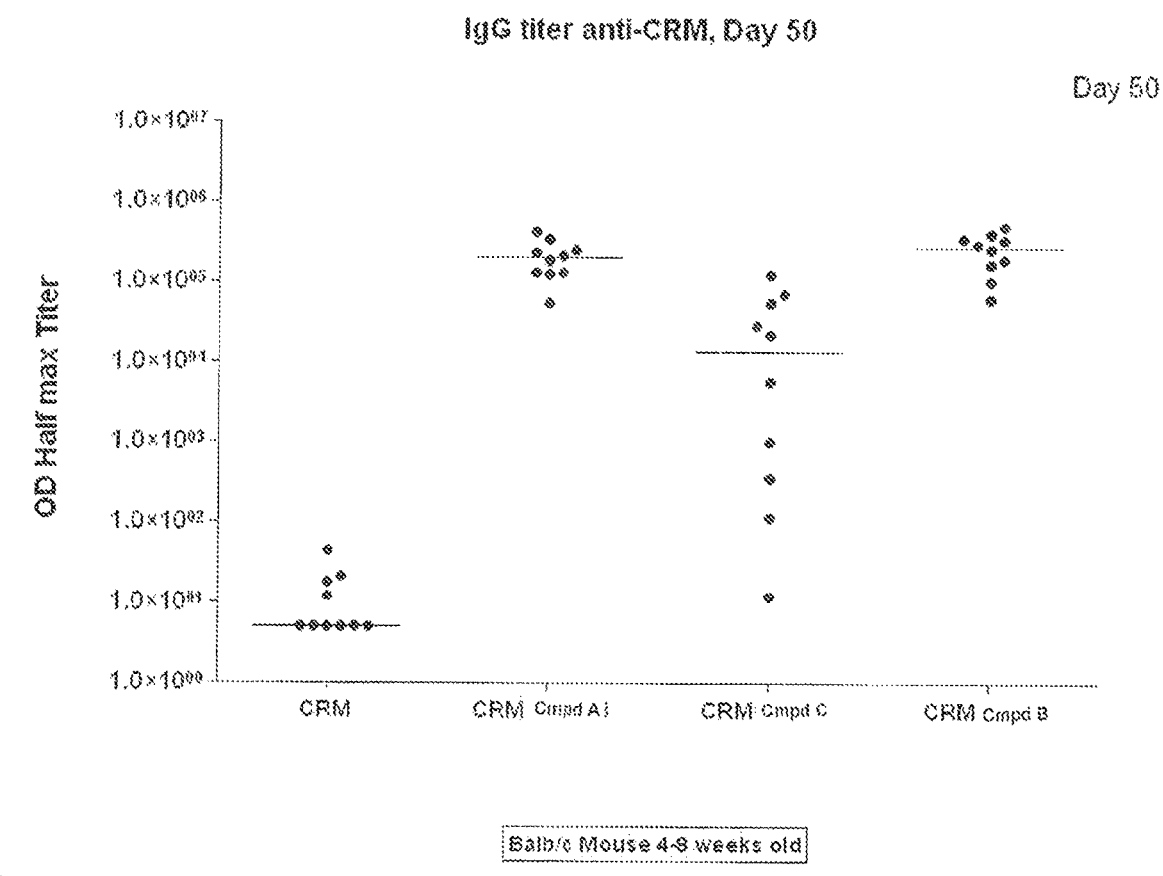
Figure 11b: CRM-specific antibody level at 7 days post 3rd injection Immunogenicity shows that CRM-Compound B conjugates and CRM-Compound A are immunogenic constructs in mice.

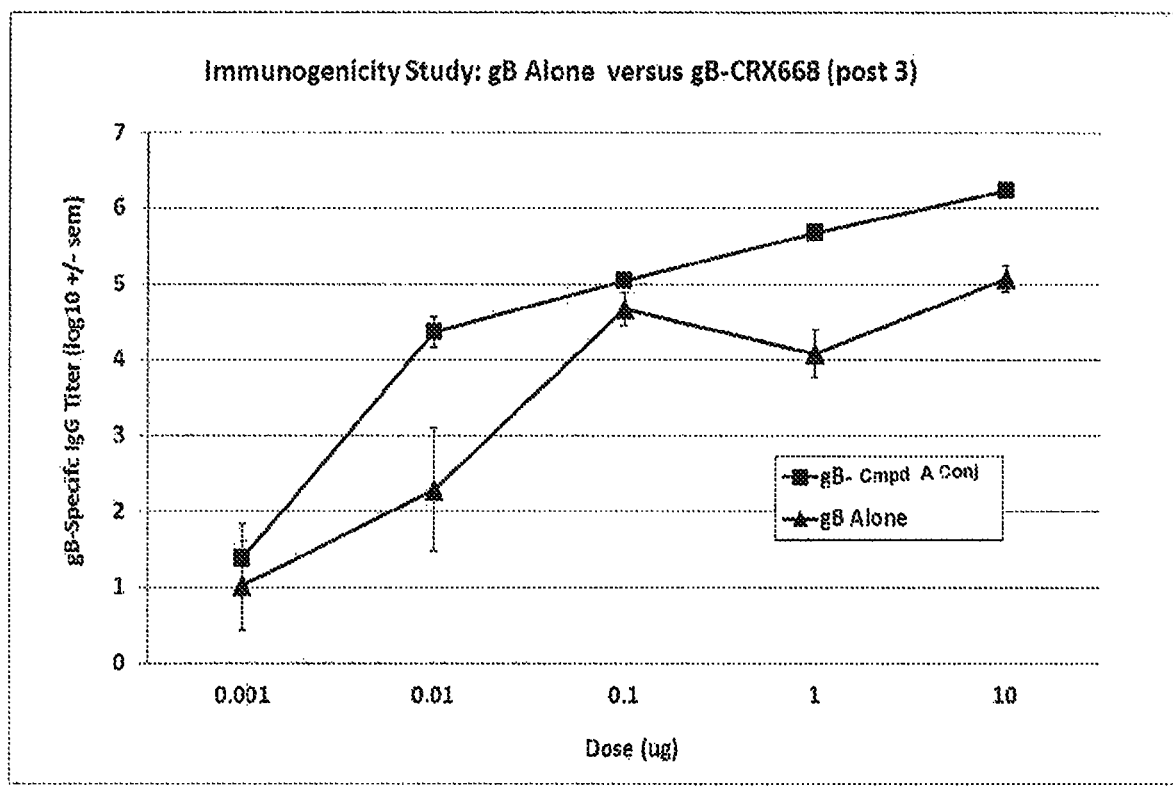
Figure 12a: gB specific IgG analysis (humoral response) from FUSION vs non-adjuvanted gB control in mice.

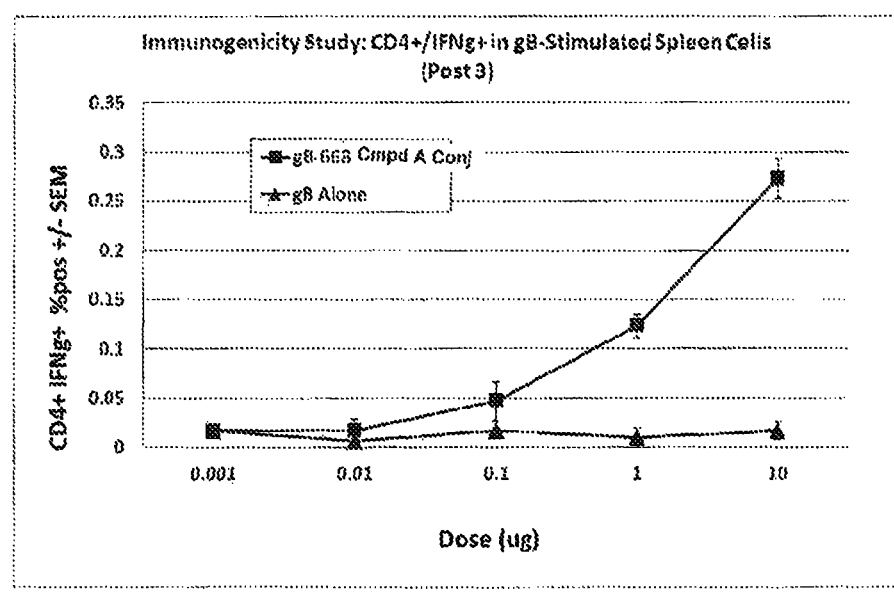
Figure 12b: Cell-mediated immunity (CMI) analysis to evaluate the CD4-IFNγ response in mice

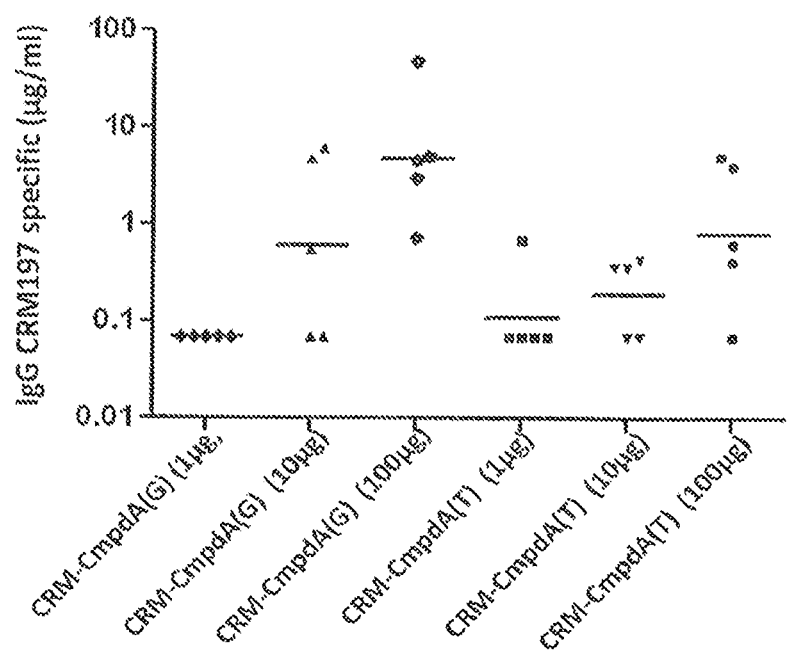
Figure 13: Dose-escalation in farm pigs to test two types of conjugates; CRM Compound A-( G) vs CRM Compound A-(T).

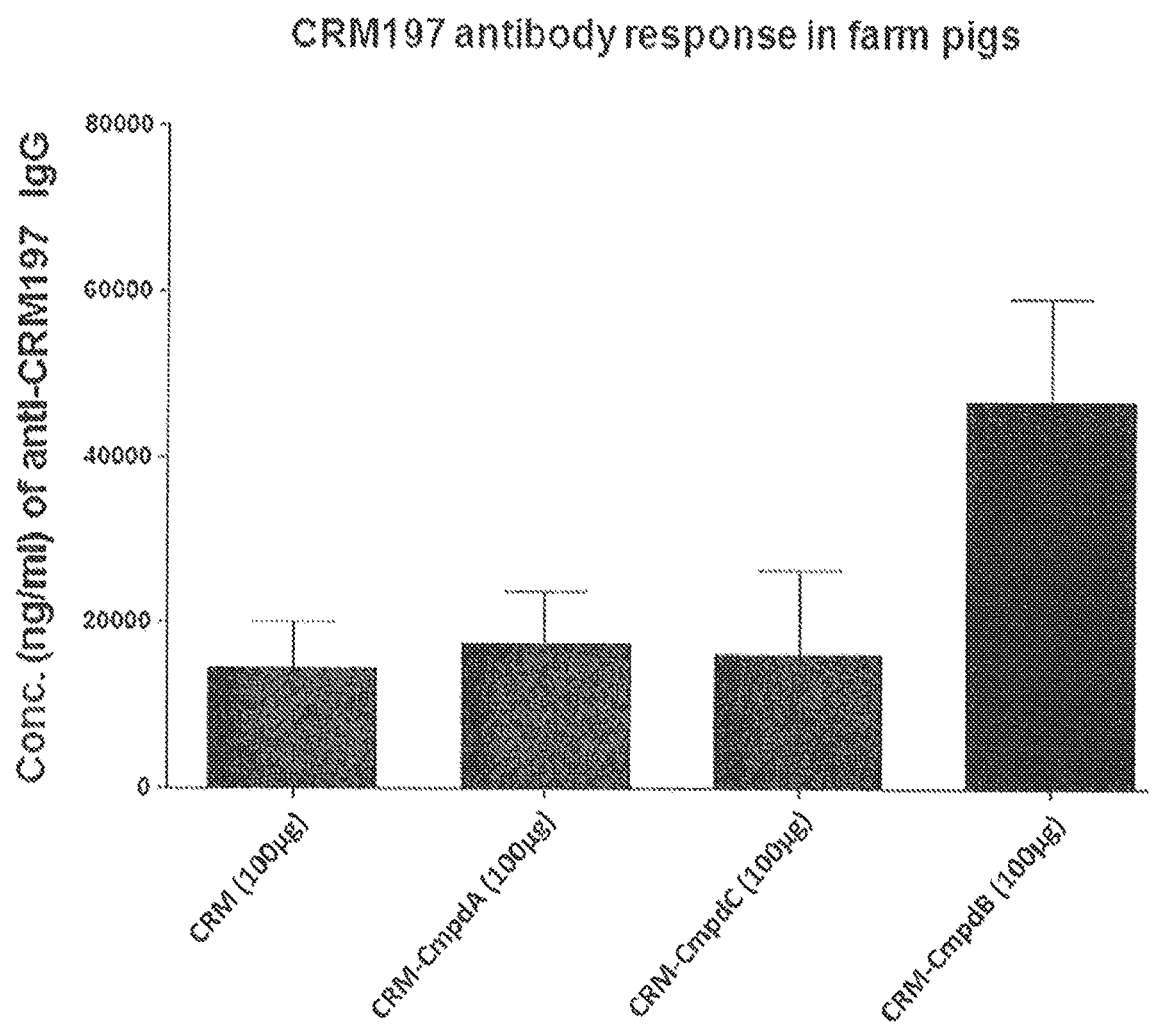
Figure 14: Testing the CRM specific humoral (antibody) response from 3 different TLR7/8 ligands conjugates in Yorkshire-Landrace-Duroc farm pigs using the intramuscular route for immunization.

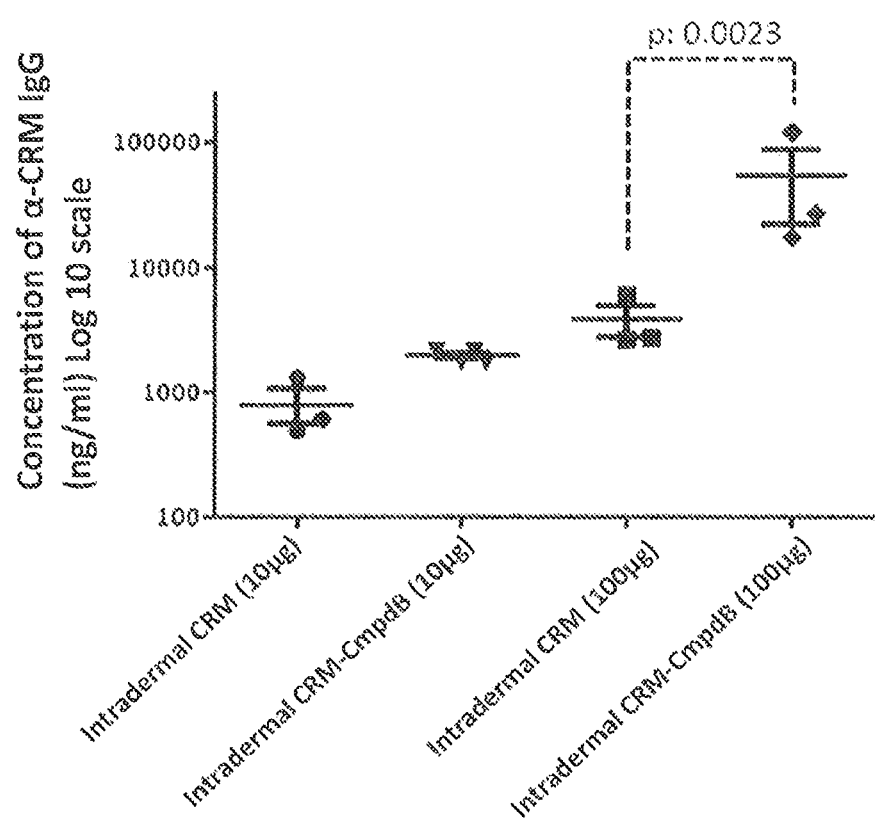
Figure 15: Antibody response of fused conjugates vs non-adjuvanted controls after intradermal immunization in farm pigs (Y

SEQUENCE LISTING

```
<160> NUMBER OF SEQ ID NOS: 1

<210> SEQ ID NO 1
<211> LENGTH: 546
<212> TYPE: PRT
<213> ORGANISM: Varicella zoster

<400> SEQUENCE: 1
```

```
Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
            35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
                100                 105                 110

Arg Leu Met Gln Pro Thr Gln Met Ser Ala Gln Glu Asp Leu Gly Asp
            115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
                180                 185                 190

Gly Val Arg Tyr Thr Glu Thr Trp Ser Phe Leu Pro Ser Leu Thr Cys
            195                 200                 205

Thr Gly Asp Ala Ala Pro Ala Ile Gln His Ile Cys Leu Lys His Thr
    210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
                260                 265                 270

Glu Leu Glu Leu Asp Pro Pro Glu Ile Glu Pro Gly Val Leu Lys Val
            275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
                340                 345                 350

Val Gly Asp Thr Phe Ser Leu Ala Met His Leu Gln Tyr Lys Ile His
            355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
```

-continued

```
            420             425             430
Glu His Ala Asp Asn Tyr Thr Ala Tyr Cys Leu Gly Ile Ser His Met
        435             440             445

Glu Pro Ser Phe Gly Leu Ile Leu His Asp Gly Gly Thr Thr Leu Lys
        450             455             460

Phe Val Asp Thr Pro Glu Ser Leu Ser Gly Leu Tyr Val Phe Val Val
465             470             475             480

Tyr Phe Asn Gly His Val Glu Ala Val Ala Tyr Thr Val Val Ser Thr
            485             490             495

Val Asp His Phe Val Asn Ala Ile Glu Glu Arg Gly Phe Pro Pro Thr
            500             505             510

Ala Gly Gln Pro Pro Ala Thr Thr Lys Pro Lys Glu Ile Thr Pro Val
        515             520             525

Asn Pro Gly Thr Ser Pro Leu Ile Arg Tyr Ala Ala Trp Thr Gly Gly
        530             535             540

Leu Ala
545
```

COMPOSITIONS AND USES

STATEMENT REGARDING FEDERALLY SPONSORED RESEARCH

This invention was made with Government support under Contract No. HHSN272200900036C awarded by the National Institutes of Health. The Government has certain rights in the invention.

The foregoing amendments are necessitated by 35 U.S.C. § 202(c)(6) and 37 CFR § 1.77(b)(I)-(3). No new matter has been added.

TECHNICAL FIELD OF THE INVENTION

The present invention relates to immunogenic compositions and methods for creating self-adjuvanted vaccines and self-adjuvanted immunotherapies comprising antigen-adjuvant conjugates and methods for producing them. More particularly, the invention relates to an immunogenic composition comprising a protein antigen cross linked to an oxoadenine adjuvant.

BACKGROUND

Effective and safe adjuvants are used to make subunit vaccines and immunotherapies sufficiently immunogenic. Simple mixing of an adjuvant with subunit vaccines or with immunotherapies often requires adding quantities of adjuvant that may lead to unwanted side-effects. Such mixing may require highly demanding and costly process development and product characterization, lead to poor shelf-life duration, or result in an inability to freeze or lyophilize the final product. Moreover, adjuvant dosing requirements may lead to re-instatement of unwanted side-effects. Accordingly, there is a need to improve the effectiveness of adjuvanted subunit vaccines and immunotherapies.

For optimal antigen presentation to T cells, antigens and adjuvants must not only be taken up by the same antigen presenting cell, but they need to be taken up by the same phagosome (Medzhitov, Nature 2006, Vol. 440). Conventional antigen/adjuvant mixtures often require large amounts of adjuvant to ensure that both are phagocytosed simultaneously. Excess adjuvant leads to overt reactogenicity that limits the usefulness of such adjuvant systems.

SUMMARY OF THE INVENTION

In a first aspect there is provided an immunogenic composition comprising an oxoadenine compound linked to an antigen The oxoadenine compound is suitably a 1 methyl butoxy oxoadenine having a piperidinyl substituent. Oxoadenine compounds of the present invention and methods for their synthesis of oxoadenine compounds are disclosed in WO2010/018134.

In a one aspect, oxoadenine compound comprises formula (I):

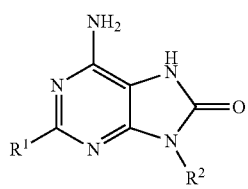

wherein;

$R^1$ is branched or saturated $C_{1-6}$alkoxy;
$R^2$ is a group having the structure:

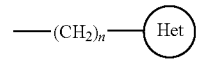

n is an integer having a value of 1 to 6; and
Het is a 6-membered saturated heterocycle containing one nitrogen atom wherein Het is attached to the —$(CH_2)_n$— moiety at any carbon atom of the heterocycle;

or a pharmaceutically acceptable salt thereof.
In a further embodiment, $R^1$ is n-butyloxy.
In a further embodiment, $R^1$ is (1 S)-1-methylbutoxy
In a further embodiment, n is 1, 2, 3, 4, 5 or 6.
4)
In one aspect of the invention the oxoadenine molecule is COMPOUND A

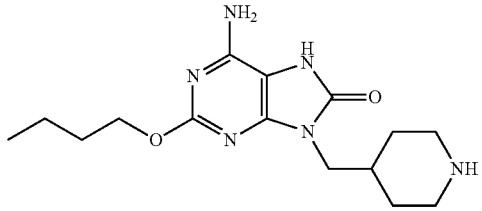 [SMILES: CCCCOc1nc(N)c2[nH]c(=O)n(CC3CCNCC3)c2n1]

In one aspect of the invention the oxoadenine molecule is COMPOUND B.

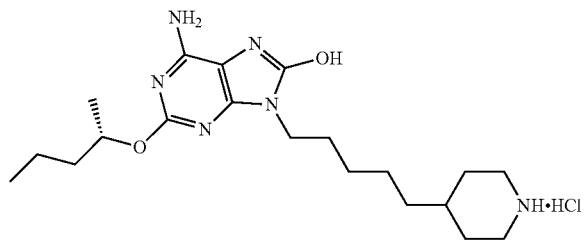

In one aspect of the invention there is provided an immunogenic composition comprising an oxoadenine compound linked to an antigen wherein the oxoadenine compound is linked to the antigen via a crosslinking agent. In one aspect of the invention the cross linking agent linked to the oxoadenine is a hydrophillic compound.

In another aspect of the invention, the addition of the crosslinking agent to the oxoadenine increases the aqueous solubility of the oxoadenine compared to to the solubility in the absence of the crosslinking agent.

In another aspect of the invention, the activated oxoadenine is more water soluble than an inactivated oxoadenine.

In another aspect of the invention the increased aqueous solubility of the activated oxoadenine provided by the crosslinking agent decreases the amount of undesired aggregate in antigen-adjuvant conjugate composition, compared to activated oxoadenine not exhibiting increased solubility.

In one aspect the crosslinking agent linked to the oxoadenine is a charged compound.

In one aspect the crosslinking agent is an amine-to-sulfhydryl crosslinker.

In one aspect the crosslinking agent contains N-Hydroxysuccinmide ester (NHS-ester) and maleimide reactive groups at opposite ends of the crosslinking agent.

In one aspect the crosslinking agent linked to the oxoadenine is GMBS,(N-gamma-Maleimidobutyryl-oxysuccinimide ester)

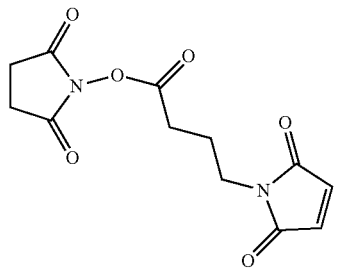

Hetero-Bifunctional Crosslinker GMBS

In one aspect the crosslinking agent GMBS is initially reacted with and activates the oxoadenine.

In one aspect the crosslinking agent GMBS is initially reacted with and activates the antigen.

In another aspect the crosslinking agent comprises Traut's reagent (2-Iminothiolane).

Traut's Crosslinking Reagent (2 Iminothiolane HCl)

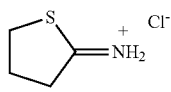

In one aspect the crosslinking agent GMBS is linked to the oxoadenine via Traut's reagent.

In a particular aspect the crosslinking agent has the following structure:

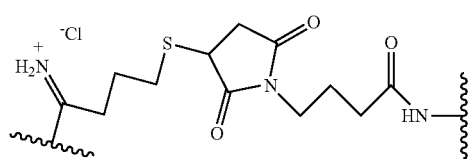

In one aspect the antigen is directly conjugated to the GMBS and the adjuvant is directly conjugated to the Traut's reagent (referred to herein as "T chemistry")

Compound B+2 Iminothiolane

In another aspect, the adjuvant is directly conjugated to GMBS while the antigen is directly conjugated to the Traut's reagent (referred to herein as "G chemistry").

When crosslinked to form the antigen-adjuvant conjugate, the conjugate can be described as having the following G or T chemistries:

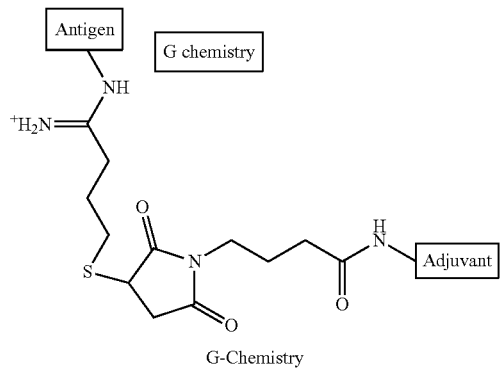

G-Chemistry

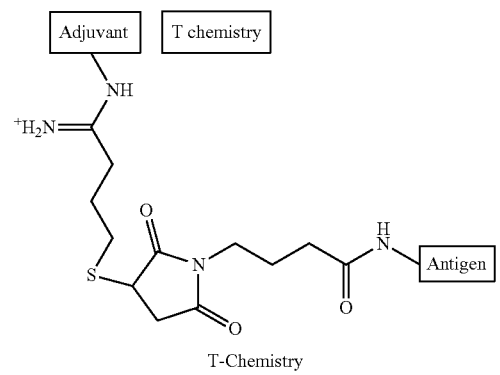

T-Chemistry

In one aspect of the invention an antigen is conjugated to the oxoadenine through the crosslinker. In the context of the present invention, the antigen conjugated to the adjuvant through the crosslinker induces an antigen specific response when administered to a subject, and in a particularly suitable aspect of the invention, the immunogenic composition induces a specific immune response in the absence of other additional adjuvant (e.g. alum), in one aspect a clinically significant specific immune response In one aspect of the invention the antigen is a diphtheria toxin antigen, and in a particular aspect of the invention, Cross Reactive Material 197 ("CRM" 197).

In another aspect of the invention the antigen is a cytomegalovirus ("CMV") antigen, and in a particular aspect of the invention a CMV gB antigen In another aspect of the invention the antigen is a cytomegalovirus ("CMV") antigen, and in a particular aspect of the invention the CMV gB antigen LVL759.

In another aspect of the invention the antigen is a Hepatitis B antigen, and in a particular aspect of the invention a Hepatitis B surface antigen ("HBsAg").

In another aspect of the invention the antigen is a varicella or varicella-zoster ("VZV") antigen, and in a particular aspect of the invention a VZV gE antigen.

In another aspect of the invention the antigen is a cancer tumor antigen, and in a particular aspect of the invention MAGE antigen or a PRAME antigen.

In another aspect of the invention the antigen is an influenza virus antigen, and in a particular aspect of the invention an HA antigen.

In another aspect of the invention the antigen is an HIV antigen, and in a particular aspect of the invention HIV gag antigen or HIV env antigen In another aspect of the invention the oxoadenine molecule is linked to the antigen via a crosslinking agent and wherein the crosslinking agent is a hydrophillic compound and preferrably thereby increases the aqueous solubility of the oxoadenine compared to to the solubility in the absence of the crosslinking agent.

In another aspect, the invention comprises an oxoadenine activated for the purpose of crosslinking wherein the activated oxoadenine is more water soluble than an unactivated oxoadenine.

In another aspect of the invention an activated oxoadenine having increased aqueous solubility provided by the crosslinking agent thereby decreases the amount of undesired aggregate in the immunugenic composition, compared to activated oxoadenine not exibiting increased solubility.

In another aspect of the invention, the number of adjuvant molecules conjugated to a antigen (the "copy number") for the population of antigen-adjuvant conjugates in the immunogenic composition is within a desired range, in particular between 3 and 6 molecules of adjuvant conjugated to an antigen, where the copy number represents the "approximate average" of the actual number of immunoeffectors per antigen molecule of a formulation.

In another aspect of the invention a first immunogenic composition comprising the antigen-adjuvant conjugate induces an increased immune response when compared with a second immunogenic composition having equal amounts of antigen and adjuvant as in the first immunogenic composition, but in which the adjuvant and adjuvant are not conjugated to each other (e.g. the adjuvant and antigen are admixed).

The terms "aspects" of the invention and "embodiments" of the invention have the same meaning, are used interchangeably herein and are intended to signify an additional but non-limiting description of the invention.

BRIEF DESCRIPTION OF THE DRAWINGS

FIG. 2. MALDI-TOF MS of an antigen (1), the antigen conjugated to GMBS (2) and the antigen conjugated to an adjuvant (3). The shifts in molecular weight indicate an average of 11 copies of GMBS per antigen and an average of 3 copies of adjuvant per antigen.

FIG. 3. SDS-PAGE of an antigen and antigen-adjuvant conjugate using a 10% Bis-Tris gel. The gel shows an increase in molecular weight of the antigen-adjuvant conjugate in lane 3 compared to the unconjugated antigen in lane 2.

FIG. 4. RP-HPLC chromatogram showing the control antigen (top), the antigen-adjuvant conjugate prior to purification by anion exchange (middle) and the final antigen-adjuvant conjugate after purification (bottom). Small amounts of free unconjugated adjuvant were observed with a retention time of 10.2 minutes in the pre anion exchange sample (middle) which were removed after anion exchange (bottom).

FIG. 5. SEC-HPLC chromatogram of an antigen (top) and antigen-adjuvant conjugate (bottom) showing a showing a small amount of dimer in the conjugate (<5%).

FIG. 6: Data showing RP-HPLC of fractions collected during ion exchange chromatography of a Compound B conjugate FIG. 7 TLR7 activation at very low doses by CRM-Compound A Lower Copy and CRM-Compound A Higher Copy using the TLR7/NF-kB/SEAP Stable Reporter Cell Line by Imgenex. CRM-Compound A conjugates (Lower Copy or Higher Copy number) do activate human TLR7 pathway as efficiently as Compound A alone.

FIG. 8 Dose-escalation study of COMPOUND A-CRM showing that a dose-response in term of CRM-specific IgG is observed from CRM-COMPOUND A conjugates in 2 different origins of BALB/c mice using T chemistry and G chemistry.

FIG. 9: Proof-of-concept study in mice showing that antigen-adjuvant conjugates induce a significant humoral response based on CRM197 specific antibody FIG. 10a: Proof-of-concept study in mice showing that CRM-Compound B fused conjugates are more efficient even with 10× less of adjuvant to mount a significant humoral response based on CRM197 specific antibody.

FIG. 10b: T cell activation assessment from splenocytes coming from immunized mice shows that the CRM-Compound B fused conjugate trigger a higher CRM197 specific T cell activation compared to CRM+Compound B Admix at 1× or 10× concentration.

FIGS. 11a and 11b: CRM-specific antibody levels at 7 days post $2^{nd}$ and post $3^{rd}$ injection; Immunogenicity shows that the described CRM-oxoadenine is a potent antigen-adjuvant conjugate.

FIG. 12a: gB specific IgG analysis (humoral response) from gB conjugate vs non-adjuvanted gB control in mice.

FIG. 12b: Cell-mediated immunity (CMI) analysis to evaluate the CD4-IFNγ response in mice FIG. 13: Dose-escalation in farm pigs to test two types of conjugates CRM-Compound A-(G) vs CRM-Compound A (T).

FIG. 14: Testing the CRM specific humoral (antibody) response from 3 different TLR7/8 ligands conjugates in Yorkshire-Landrace-Duroc farm pigs using the intramuscular route for immunization.

FIG. 15: Antibody response of fused conjugates vs non-adjuvanted controls after intradermal immunization in farm pigs (Yorkshire-Landrace).

DETAILED DESCRIPTION

Figure 1:
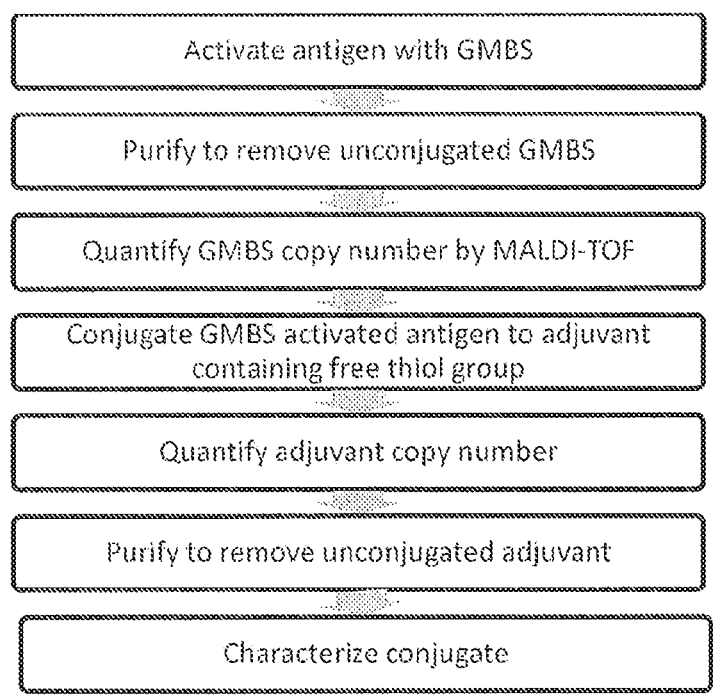
FIG. 1 Process flow diagram of T-chemistry, an antigen activated with GMBS conjugated to adjuvant.

The present invention is described in terms known and appreciated by those skilled in the art. For ease of reference certain terms hereinafter are defined. The fact that certain terms are defined, however, should not be considered as indicative that defined terms are used in a manner inconsistent with the ordinary meaning or, alternatively, that any term that is undefined is indefinite or not used within the ordinary and accepted meaning. Rather, all terms used herein are believed to describe the invention such that one of ordinary skill can appreciate the scope of the present invention. The following definitions are meant to clarify, but not limit, the terms defined.

References to 'alkyl' include references to both straight-chain and branched-chain aliphatic isomers of the corresponding alkyl containing up to eight carbon atoms, for example up to six carbon atoms, or up to four carbon atoms, or up to two carbon atoms, or one carbon atom. Such references to 'alkyl' are also applicable when an alkyl group is part of another group, for example an alkylamino or alkoxy group. Examples of such alkyl groups and groups containing alkyl groups are $C_{1-8}$ alkyl, $C_{1-6}$alkyl, $C_{1-6}$alkylamino, and $C_{1-6}$alkoxy.

References to 'heterocycle' or 'heterocyclyl' refer to a monocyclic saturated heterocyclic aliphatic ring containing carbon atoms and one heteroatom, which heteroatom is nitrogen. Such a heterocyclic ring is piperidine or piperidinyl.

In a first aspect there is provided an immunogenic composition comprising an oxoadenine compound linked to an antigen wherein the oxoadenine is substituted at the $C_9$ position with a piperidinylalkyl moiety.

Oxoadenine compounds of the present invention and methods for their synthesis are disclosed in WO2010/018134.

A compound of Formula I

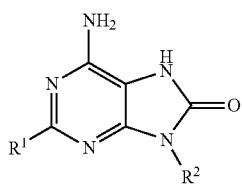

(I)

wherein;

$R^1$ is branched or saturated $C_{1-6}$alkoxy;

$R^2$ is a group having the structure:

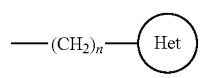

n is an integer having a value of 1 to 6; and

Het is a 6-membered saturated heterocycle containing one nitrogen atom wherein Het is attached to the —(CH$_2$)$_n$— moiety at any carbon atom of the heterocycle; or pharmaceutically acceptable salts thereof.

4)
Examples of oxoadenine compounds include:

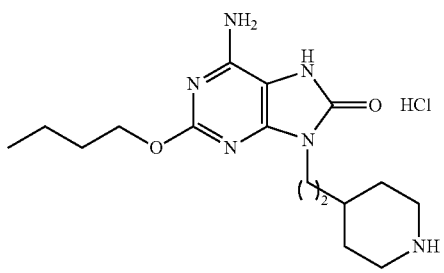

8 CRX-672

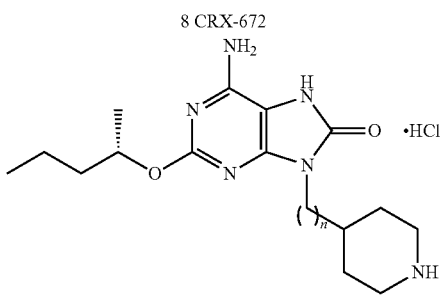

9 n = 1 CRX-692
10 n = 5 CRX-725

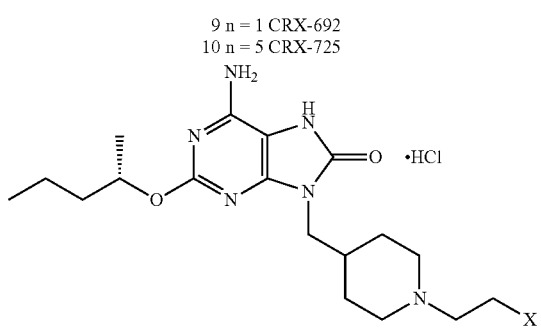

11 X = OH (CRX-748)
12 X = NH$_2$ (CRX-753)

In one particular embodiment the oxoadenine compound is COMPOUND A

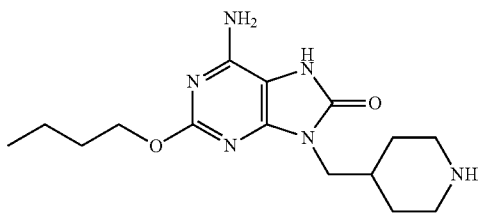 [SMILES: CCCCOc1nc(N)c2[nH]c(=O)n(CC3CCNCC3)c2n1]

In another particular embodiment, the oxoadenine compound is Compound B.

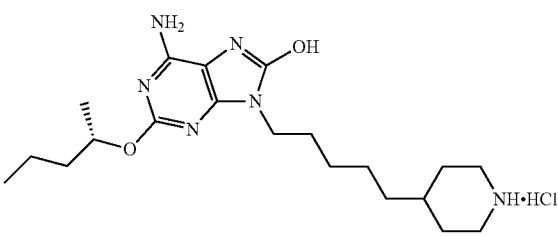

Conjugation

Oxoadenine compounds are known to act as immunopotentiators and/or adjuvants. These oxoadenine compounds are covalently coupled to antigens such as, for example, CRM197 (inactivated by mutation 197 in the diphtheria toxin) or recombinant gB (from human cytomegalovirus). Numerous chemistries are available for crosslinking of amines and thiol containing molecules (see Hermanson 2$^{nd}$ Edition). Several other classes of heterobifunctional crosslinking agents may be used to control the positioning of TLR agonists on the antigen based on reaction site and linker length/composition. Employing different conjugate strategies may produce more effective or less effective responses; the conjugation strategy must be carefully selected to yield the desired activity.

Alternate strategies are disclosed herein. In one strategy, referred to as the G-chemistry process, the antigen protein fragment is reacted with a cross linking nucleophile (a linker, e.g., Traut's reagent). The oxoadenine compound is activated with a complementary cross linking electrophile (e.g. GMBS) and subsequently added to the activated antigen to complete the conjugation.

In an alternative strategy, the T-chemistry process, the TLR agonist (e.g. COMPOUND A) is reacted with a cross linking reagent or linker (e.g. Traut's reagent). Then, the TLR and attached cross linking material is reacted with the antigen activated with GMBS.

More specifically in the T-chemistry process, representing one embodiment of the present invention, In one aspect, GMBS links to the antigen via an amide bond and the antigen-GMBS conjugate is then purified to remove any unconjugated GMBS. The copy number of GMBS per antigen is then determined using mass spectrometry techniques. Next the GMBS-activated antigen is conjugated to the adjuvant via free thiol group on the adjuvant. The free thiol may be part of the oxoadenine or modified oxoadenine structure. Alternatively, the free thiol may also be added to the oxoadenine core, such as through the use of a crosslinking reagent (e.g. Traut's reagent). The copy number of adjuvant molecules crosslinked to the antigen is determined and the composition is purified and characterized. FIG. 1 (flow chart).

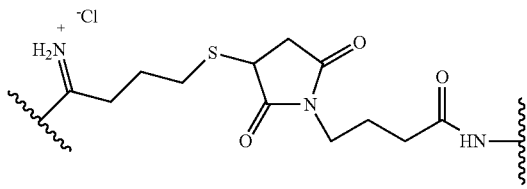

More particularly, the T-chemistry may involve:
(i) adjusting the pH of the antigen protein fragment with a buffer such as a Good's Buffer (e.g., bicine) to a pH greater than 7,
(ii) (ii) activating the buffered antigen protein fragment having a pH greater than 7 with a crosslinker (e.g., GMBS);
(iii) (iii) removing excess crosslinker (GMBS) by means of purifying centrifugal ultrafiltration;
(iv) conjugating with an excess of adjuvant-cross linking material (e.g. Compound A-Traut's);
(v) removing the excess of TLR-cross linking material by purifying centrifugal ultrafiltration and/or ion exchange chromatography (vi) filtering with a PVDF syringe filter to produce a sterile conjugated protein of the invention.

Additionally protective groups may be required to prevent dimerization of the activated peptide, for example, capping free thiols on the antigen when the process employs conjugation via thiol linkage.

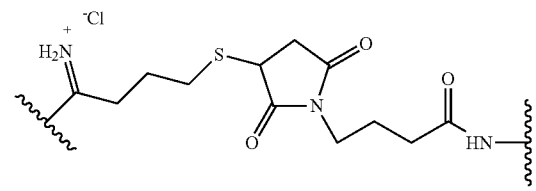

Purification by Ion Exchange Chromatography:

In cases where the limited solubility of the adjuvant or adjuvant-linker (Traut's) prevents complete purification of unconjugated adjuvant by ultrafiltration it may be necessary to use ion exchange chromatography to remove the remaining adjuvant.

In yet another aspect, a protein antigen is conjugated to an oxoadenine (e.g. COMPOUND A) in accordance with "T-chemistry" by carrying out the following steps:
Step 1 Protein pH adjusted to 7.4
Step 2 GMBS pre-dissolved in DMSO to ~1 mg/mL
Step 3 Protein equilibrated to 25° C.
Step 4 Necessary Equivalents of GMBS added to Protein
Step 5 Vortex 10 seconds to mix
Step 6 allow activation to proceed 0.5 h at 25° C. protein transferred to 15 mL Amicon centrifugation
Step 7 tube MWCO 30 kD
Protein washed 3× with 15 mL each time using 20 mM
Step 8 Bicine pH=7.4, 0.15M NaCl buffer
Protein reconstituted to 0.5 mg/mL in wash buffer and
Step 9 an aliquot taken for MALDI-TOF MS
COMPOUND A-Trts reagent was prepared by dissolving COMPOUND A in DMF/H$_2$O (9:1) at 25 mg/ml and adding 1 equivalent of 2-iminothiolane dissolved in DMF/H$_2$O (9:1) at 25 mg/ml and 2.5 equivalents of diisopropylethylamine. The reaction was allowed to incubate at 25° C. for 45 minutes and was
Step 10 tested by LCMS to monitor the reaction
Equivalents of Compound A-Traut's added to activated
Step 11 protein and vortexed for 10 seconds to mix
Step 12 Conjugation allowed to proceed at room temp
At t=2 h an aliquot was taken and checked by MALDI-TOF MS to determine how many copies of Compound
Step 13 A added to protein.
Compound A Copy # was sufficient so reaction solution transferred to 15 mL Amicon centrifugation tube
Step 14 MWCO 30 kD
Protein washed 5× with 15 mL each time using 20 mM
Step 15 Bicine pH=7.4, 0.15M NaCl buffer
Protein reconstituted to 0.5 mg/mL in wash buffer and an aliquot taken for MALDI-TOF MS and HPLC
Step 16 analysis
Conjugate was sterile filtered using a 0.22 micron
Step 17 PVDF filter
Step 18 Conjugate placed in 2-8° C. storage In the process, free thiols may cause dimer and trimer formation. To control the occurrence of free thiols and thus minimize the formation of dimers and trimers, free thiols are capped with IAA or NHM as follows:
1. Cap free thiols in antigen (e.g. gB) by treating for 10 min with IAA, or NHM then purify away excess by ultrafiltration
2. Activate with 20 to 40 equivalents of GMBS, react 30 min at RT
3. Purify away excess GMBS by centrifugal ultrafiltration 30 kD MWCO
4. Conjugate with 20 molar excess of 668-traut's for 2-12 hours
5. Purify away excess Compound A-Traut's by centrifugal ultrafiltration 30 kD MWCO
6. Sterile filter with 0.22 um PVDF syringe filter
7. Characterization of conjugates by MALDI-TOF, RP and SEC-HPLC, LAL, and BCA Reaction conditions (time, stoichiometry, base) may vary depending on the adjuvant being conjugated and the reactivity of the primary/secondary amine, HCl salt vs free base, solubility, etc. Reaction conditions and purification methods may also vary depending on antigen properties including the sequence, stability, size, solubility etc.

COPY Number

In one embodiment, an oxoadenine compound is covalently linked to the CRM197 molecule with three molecules of oxoadenine per antigen CRM molecule. The number of copies of oxoadenine conjugated can be controlled by multiple variables. For example, in the case of GMBS crosslinking, some of the variables that provide control over the copy number are: the excess of GMBS used to react with antigen, reaction temperature, buffer type, reaction concentration, reaction pH and lastly, the excess of activated oxoadenine during the final addition step. The stoichiometric relationship of the adjuvant molecules to antigen is determined using techniques known in the art and in one aspect of the invention, by using mass spectrometry. The number of adjuvant molecules conjugated to antigen will typically be varied for any given number of molecules. In one aspect of the invention the number of adjuvant molecules conjugated to antigen will be present as a Gaussian distribution. In another aspect of the invention, in a majority of the antigen-adjuvant conjugates in a composition the ratio of antigen to adjuvant molecules is the copy number. Therefore the term "copy number" and the stoichiometric relationship of immunostimulator/immunopotentiator compounds to antigen as measured by mass spectrometry or other methods represents an average of the actual number of immunoeffectors per antigen molecule of a formulation.

In one aspect of the invention the average copy number is 1, 2, 3, 4, 5 or 6 or between 1 to 6, 2 to 5, and 3 to 4 molecules of oxoadenine per antigen molecule.

Antigens

Immunogenic formulations of the present invention comprise one or more antigens. In some aspects of the invention an immunogenic composition may comprise more than one type of antigen wherein all the antigens are conjugated to an adjuvant whereas in another aspect an immunogenic composition may comprise more than one type of antigen wherein at least one type of antigen is conjugated to an adjuvant, but another type antigens may not be conjugated. In one aspect of the invention, such antigens may be selected from the group consisting of: diphtheria, Hepatitis B surface antigen, glycoprotein b (gB) of cytomegalovirus (CMV) and glycoprotein E (gE) of varicella-zoster virus (VZV). When being administered, antigens will typically be present at a final concentration of at least 1 μg/mL each, for instance 1 μg/mL or within the ranges of 1-20 μg/mL, 2-15 μg/mL, 2.5-10 μg/mL, 3-8 μg/mL, or 4-6 μg/mL or of 5 μg/mL. Additionally in another aspect of the invention, antigens could be present a broader range of final concentration such 1-200 μg/mL and 1-50 μg/mL. In general, the concentration of any antigen will be sufficient to elicit an immune response against that antigen. It is preferred that the protective efficacy of individual antigens is not removed by combining them, although actual immunogenicity (e.g. ELISA titers) may be reduced.

While at least one of the antigen(s) in the immunogenic composition is conjugated to an adjuvant in accordance with the present invention, in another embodiment of the invention other additional antigens are not so conjugated. For example, in one immunogenic composition of the present invention, a first antigen is conjugated to an oxoadenine adjuvant, while a second different antigen in the immunogenic composition is not conjugated to an oxoadenine adjuvant. In such embodiments the additional antigen may be free or, by way of example, may be adsorbed onto a particle or carrier, such as being adsorbed onto an aluminium salt, such as aluminium hydroxide or aluminium phosphate or onto a mixture of both aluminium hydroxide and aluminium phosphate.

Antigens of the present invention will typically be protein antigens. Antigens in immunogenic compositions of the invention will be present in "immunologically effective amounts" i.e. the administration of that amount to an individual, either in a single dose or as part of a series, is effective for treatment or prevention of disease. Dosage treatment may be a single dose schedule or a multiple dose schedule (e.g. including booster doses).

Antigen Fraqment(s).

Antigen (abbreviated as "Ag" herein) fragments employed in the present invention typically have certain properties useful in conjugation. In one aspect, the antigen fragments are proteins that are stable in solution and not prone to any substantial aggregation. In another aspect the antigen fragment contains a minimum of three available amines at which conjugation can occur and have a size of less than 500 kD. In another aspect the preferred characteristics or properties include: an antigen fragment solubility greater than 1 mg/mL, a monomer or oligomer (preferably a monomer), and a size of less than 150 kD.

Such fragments are readily commercially available and/or can be readily made by those skilled in the ar. Antigen fragments that can be employed in the invention include, for example, those set forth in Table 1 below.

TABLE 1

| Antigen | MW (KD) | Monomer | Solubility/Stability | Other |
| --- | --- | --- | --- | --- |
| CRM-197 | 58 | monomer | 4 mg/mL/years | — |
| Tetanus Toxoid | 150 | monomer | 30 mg/mL/years | — |
| HA | 60 | homotrimer | — | — |
| gB of CMV virus | 93 | trimer | — | glycosylated |
| preF | 60 | trimer | — | glycosylated |

TABLE 1-continued

| Antigen | MW (KD) | Monomer | Solubility/Stability | Other |
|---|---|---|---|---|
| Hash-2 | 20 | monomer | — | — |
| HPV E7 | 11 | — | — | — |
| Pertussis toxin (PT) | approx. 105 | 5 subunits | * | — |
| HBs (S antigen) | — | — | — | e.g. VLP |
| Ovalbumin | | | | |
| MAGEA3 | | | | |

* before detox: store at 20 degrees C in glycerol; after detox: a month at 4 degrees C.

In some aspects of the invention, antigen candidates may include pertussis antigens, tetanus antigens rhinovirus antigens, TB antigens, allergy antigens, and malaria antigens.

CRM197

The present invention may comprise a diphtheria antigen, such as a diphtheria toxoid. The preparation of diphtheria toxoids (DT) is well documented. Any suitable diphtheria toxoid may be used. For instance, DT may be produced by purification of the toxin from a culture of *Corynebacterium diphtheriae* followed by chemical detoxification, but is alternatively made by purification of a recombinant, or genetically detoxified analogue of the toxin (for example, CRM197, or other mutants as described in U.S. Pat. Nos. 4,709,017, 5,843,711, 5,601,827, and 5,917,017).

In one aspect of the invention, CRM197 is a non-toxic form of the diphtheria toxin but is immunologically indistinguishable from the diphtheria toxin. CRM197 is produced by *C. diphtheriae* infected by the nontoxigenic phase beta197tox-created by nitrosoguanidine mutagenesis of the toxigenic carynephage b (Uchida et al Nature New Biology 233; 8-11). The CRM197 protein has the same molecular weight as the diphtheria toxin but differs from it by a single base change in the structural gene. This leads to a glycine to glutamine change of amino acid at position 52 which makes fragment A unable to bind NAD and therefore non-toxic (Pappenheimer 1977, Ann Rev, Biochem. 46; 69-94, Rappuoli Applied and Environmental Microbiology September 1983 p 560-564).

CMV gB

In one aspect of the present invention, the antigen is derived from cytomegalovirus (CMV). In a particular embodiment the antigen is gB polypeptide and suitably comprising at least a portion of a gB protein extracellular domain. The extracellular domain may further comprise a fusion loop 1 (FL1) domain and a fusion loop 2 (FL2) domain, wherein at least one of the FL1 and FL2 domains comprises at least one amino acid deletion or substitution. In another embodiment the antigen is recombinant truncated gB protein, deleted from part of the transmembrane domain, from the cytoplasmic domain, as well as part of the leader sequence, optionally in a truncated form having additional mutations in fusion loops FL1 and FL2 of gB.

It was observed that prior art gB polypeptides, such as a CMV gB polypeptide lacking the transmembrane domain, presented heterogeneity in the N-terminal part of the polypeptide. A homogeneous population is to be understood as a population mainly made of a single mature polypeptide, the polypeptide starting unvaryingly with an identical given amino acid at the N-terminal end. In the present invention, a "mature" polypeptide refers to a polypeptide wherein the signal sequence has been cleaved off. In the present invention, in a N-terminal homogeneous population, more than 30%, suitably at least 80%, more suitably from 80% to 90%, more suitably at least 99% of the mature polypeptides produced after cleavage of the signal sequence start with the same amino acid at the N-terminal end. Accordingly, in one embodiment, there is provided a preparation comprising a population of mature CMV gB polypeptides produced after cleavage of the signal sequence, wherein at least 30%, at least 80%, from 80% to 90% of the mature gB polypeptides comprise the same amino acid at the N-terminal end. In particular, the mature polypeptides of the invention suitably start with a serine or a histidine at the N-terminal position.

HBsAg

The envelope of the hepatitis B virus is made up of a protein known as hepatitis B surface antigen, and contains two other antigens known as pre-S1 and pre-S2 antigens. The core of the virus contains two other proteins that act as antigens—the 'e' antigen and the core antigen. In one particular embodiment the antigen is a hepatitis B antigen, preferably hepatitis B surface antigen (HBsAg). The preparation of Hepatitis B surface antigen (HBsAg) is well documented. See for example, Harford et al in *Develop. Biol. Standard* 54, page 125 (1983), Gregg et al in *Biotechnology*, 5, page 479 (1987), EP-A-0 226 846, EP-A-0 299 108 and references therein.

As used herein the expression 'Hepatitis B surface antigen' or 'HBsAg' includes any Hepatitis B surface antigen' or fragment thereof displaying the antigenicity of HBV surface antigen. It will be understood that in addition to the 226 amino acid sequence of the HBsAg S antigen (see Tiollais et al, Nature, 317, 489 (1985) and references therein) HBsAg as herein described may, if desired, contain all or part of a pre-S sequence as described in the above references and in EP-A-0 278 940. HBsAg as herein described can also refer to variants, for example the 'escape mutant' described in WO 91/14703. In a further aspect the HBsAg may comprise a protein described as SL* in European Patent Application Number 0 414 374, that is to say a protein, the amino acid sequence of which consists of parts of the amino acid sequence of the hepatitis B virus large (L) protein (ad or ay subtype), characterised in that the amino acid sequence of the protein consists of either:

(a) residues 12-52, followed by residues 133-145, followed by residues 175-400 of the said L protein; or (b) residue 12, followed by residues 14-52, followed by residues 133-145, followed by residues 175-400 of the said L protein.

HBsAg may also refer to polypeptides described in EP 0 198 474 or EP 0 304 578.

In particular, the HBsAg may comprise a polypeptide comprising an amino acid sequence comprising residues 133-145 followed by residues 175-400 of the L-protein of HBsAg relative to the open reading frame on a Hepatitis B virus of ad serotype (this polypeptide is referred to as L*; see EP0414374). HBsAg within the scope of the invention may also include the preS1-preS2-S polypeptide described in EP0198474 (Endotronics) or analogues thereof such as those described in EP0304578 (McCormick and Jones) HBsAg as herein described can also refer to mutants, for example the "escape mutant" described in WO 91/14703 or EP0511855A1, especially HBsAg wherein the amino acid substitution at position 145 is to arginine from glycine.

The preparation of Hepatitis B surface antigen (HBsAg) is well documented. See for example, Hartford et al., 1983, Develop. Biol. Standard 54:125, Gregg et al., 1987, Biotechnology 5:479, EP0226846, EP0299108. It may be prepared as follows. One method involves purifying the antigen in particulate form from the plasma of chronic hepatitis B carriers, as large quantities of HBsAg are synthesised in the liver and released into the blood stream during an HBV infection. Another method involves expressing the protein by recombinant DNA methods. The HBsAg may be prepared by expression in the *Saccharomyces cerevisiae* yeast, *pichia*, insect cells (e.g. Hi5) or mammalian cells. The HBsAg may be inserted into a plasmid, and its expression from the plasmid may be controlled by a promoter such as the "GAPDH" promoter (from the glyceraldehyde-3-phosphate dehydrogenase gene). The yeast may be cultured in a synthetic medium. HBsAg can then be purified by a process involving steps such as precipitation, ion exchange chromatography, and ultrafiltration. After purification, HBsAg may be subjected to dialysis (e.g. with cysteine). The HBsAg may be used in a particulate form.

The HBsAg may be in particle form. The particles may comprise for example S protein alone or may be composite particles, for example L*, S) where L* is as defined above and S denotes the S-protein of HBsAg. The said particle is advantageously in the form in which it is expressed in yeast.

In one embodiment, HBsAg is present at an amount of 1-20 tg, 5-20 μg, 8-15 μg or approximately or exactly 10 μg per 0.5 mL dose.

In one embodiment, HBsAg is the antigen used in EngerixB™ (GlaxoSmithKline Biologicals S.A.), which is further described in WO93/24148.

VZV gE

The VZV antigen is the VZV glycoprotein gE (also known as gpl) or immunogenic derivative hereof. The wild type or full length gE protein consists of 623 amino acids comprising a signal peptide, the main part of the protein, a hydrophobic anchor region (residues 546-558) and a C-terminal tail. In one aspect, a gE C-terminal truncate (also referred to truncated gE or gE truncate) is used whereby the truncation removes 4 to 20 percent of the total amino acid residues at the carboxy terminal end. In a further aspect, the truncated gE lacks the carboxy terminal anchor region (suitably approximately amino acids 547-623 of the wild type sequence). In a further aspect gE is a truncated gE having the sequence of SEQ ID NO. 1.

The gE antigen, anchorless derivatives thereof (which are also immunogenic derivatives) and production thereof is described in EP0405867 and references therein [see also Vafai A. Antibody binding sites on truncated forms of varicella-zoster virus gpl(gE) glycoprotein Vaccine 1994 12:1265-9]. EP192902 also discloses gE and production thereof.

Truncated gE having the sequence of Seq ID NO. 1, is also disclosed by Haumont et al. Virus Research (1996) vol 40, p 199-204, herein incorporated fully by reference.

Leroux-Roels I. et al. (JID 2012:206 1280-1290) reported on a phase I/I1 clinical trial evaluating an AS01 adjuvanted VZV truncated gE subunit vaccine.

Adjuvants

As explained herein, in one aspect of the present invention, the "self-adjuvanted" antigen-adjuvant conjugates are able to induce a specific immune response in the absence of additional antigen or adjuvant. However, the use of such antigen-adjuvant conjugates in an immunogenic composition of the present invention does not preclude the use of other antigens or adjuvants in the immunogenic composition. Immunogenic compositions of the present invention may additionally include a pharmaceutically acceptable excipient, such as a suitable adjuvant. Suitable adjuvants include an aluminium salt such as aluminium hydroxide or aluminium phosphate, but may also be a salt of calcium, iron or zinc, or may be an insoluble suspension of acylated tyrosine, or acylated sugars, or may be cationically or anionically derivatised saccharides, polyphosphazenes, biodegradable microspheres, monophosphoryl lipid A (MPL), lipid A derivatives (e.g. of reduced toxicity), 3-O-deacylated MPL, synthetic mimetics MPL such as aminoalkyl glucosaminide, (AGP) quil A, Saponin, QS21, tocol (EP 0382271), Freund's Incomplete Adjuvant (Difco Laboratories, Detroit, Mich.), Merck Adjuvant 65 (Merck and Company, Inc., Rahway, N.J.), AS-2, AS-3, AS-4(Smith-Kline Beecham, Philadelphia, Pa.), MF59 (Novartis) CpG oligonucleotides, bioadhesives and mucoadhesives, microparticles, liposomes, polyoxyethylene ether formulations, polyoxyethylene ester formulations, muramyl peptides or imidazoquinolone compounds (e.g. imiquamod and its homologues) and oxoadenines. Human immunomodulators suitable for use as adjuvants in the invention include cytokines such as interleukins (e.g. IL-1, IL-2, IL-4, IL-5, IL-6, IL-7, IL-12, etc), macrophage colony stimulating factor (M-CSF), tumour necrosis factor (TNF), granulocyte, macrophage colony stimulating factor (GM-CSF) may also be used as adjuvants.

Non-Immunological Components

Immunogenic compositions of the present invention will typically, in addition to the antigenic and adjuvant components mentioned above, comprise one or more "pharmaceutically acceptable carriers or excipients", which include any excipient that does not itself induce the production of antibodies harmful to the individual receiving the composition. Suitable excipients are typically large, slowly metabolised macromolecules such as proteins, saccharides, polylactic acids, polyglycolic acids, polymeric amino acids, amino acid copolymers, sucrose (Paoletti et al., 2001, Vaccine, 19:2118), trehalose (WO 00/56365), lactose and lipid aggregates (such as oil droplets or liposomes). Such carriers are well known to those of ordinary skill in the art. The compositions may also contain diluents, such as water, saline, glycerol, etc. Additionally, auxiliary substances, such as wetting or emulsifying agents, pH buffering substances, and the like, may be present. Sterile pyrogen-free, phosphate buffered physiologic saline is a typical carrier. A thorough discussion of pharmaceutically acceptable excipients is available in reference Gennaro, 2000, Remington: The Science and Practice of Pharmacy, 20$^{th}$ edition, ISBN: 0683306472.

Compositions employing conjugates of the invention may be more readily lyophilised or amenable to spray drying than admixed counterparts or may be in aqueous form, i.e. solutions or suspensions. In some instances, liquid formulations of comprising an antigen-adjuvant conjugate as described allow the compositions to be administered direct from their packaged form, without the need for reconstitution in an aqueous medium, and are thus ideal for injection. Compositions may be presented in vials, or they may be presented in ready filled syringes. The syringes may be supplied with or without needles. A syringe will include a single dose of the composition, whereas a vial may include a single dose or multiple doses (e.g. 2 doses). In one embodiment the dose is for human. In a further embodiment the dose is for an adult, adolescent, toddler, infant or less than one year old human and may be administered by injection.

Improved adjuvant effect of the conjugates and compositions comprising the conjugates may allow for the manufacture of immunogenic compositions having reduced antigen content but yielding equivalent immunogenic effect, when compared to similar antigen and adjuvant that are not-conjugated. Formulation using the novel conjugate may thereby provide a beneficial dose-sparing effect.

Improved reactogenicity profile of the conjugates and compositions comprising the conjugates may allow for the manufacture of efficacious immunogenic compositions with reduced reactogenicity compared to compositions comprising a similar antigen and adjuvant, but that are not conjugated. For example, the reactogencity profile of the antigen-adjuvant conjugate may be improved over that of the admixed antigen and adjuvant. Similarly, the manufacture of immunogenic compositions having improved efficacy with substantially equivalent reactogenicity compared to compositions comprising a similar antigen and adjuvant, but that are not conjugated. For example, the efficacy of the antigen-adjuvant conjugate may be improved over that of the admixed antigen and adjuvant. Formulation using the novel conjugate may thereby provide an increased therapeutic window.

Immunogenic compositions of the invention may be packaged in unit dose form or in multiple dose form (e.g. 2 doses). For multiple dose forms, vials are preferred to pre-filled syringes. Effective dosage volumes can be routinely established, but a typical human dose of the composition for injection has a volume of 0.5 mL. In one embodiment, immunogenic compositions of the invention have a pH of between 6.0 and 8.0, in another embodiment immunogenic compositions of the invention have a pH of between 6.3 and 6.9, e.g. 6.6±0.2. The compositions may be buffered at this pH. Stable pH may be maintained by the use of a buffer. If a composition comprises an aluminium hydroxide salt, a histidine buffer may be used (WO003/009869). The composition should be sterile and/or pyrogen free. Immunogenic compositions of the invention may be isotonic with respect to humans.

Immunogenic compositions of the invention may include an antimicrobial. Any preservative is preferably present at low levels. Preservative may be added exogenously and/or may be a component of the bulk antigens which are mixed to form the composition (e.g. present as a preservative in antigens).

Immunogenic compositions of the present invention may comprise detergent e.g. a Tween (polysorbate), such as Tween 80. Detergents are generally present at low levels e.g. <0.01%. Immunogenic compositions of the invention may include sodium salts (e.g. sodium chloride) to give tonicity. The composition may comprise sodium chloride. In one embodiment, the concentration of sodium chloride in the composition of the invention is in the range of 0.1 to 100 mg/mL (e.g. 1-50 mg/mL, 2-20 mg/mL, 5-15 mg/mL) and in a further embodiment the concentration of sodium chloride is 10±2 mg/mL NaCl e.g. about 9 mg/mL. Immunogenic compositions of the invention will generally include a buffer. A phosphate or histidine buffer is typical. Immunogenic compositions of the present invention may include free phosphate ions in solution (e.g. by the use of a phosphate buffer) in order to favor non-adsorption of antigens.

In one embodiment the immunogenic compositions of the invention are formulated for in vivo administration to the host in such a way that the individual components of the composition are formulated so that the immunogenicity of individual components is not substantially impaired by other individual components of the composition. By not substantially impaired, it is meant that upon immunization, an antibody titre against each component is obtained which is more than 60%, 70%, 80% or 90%, or 95-100% of the titre obtained when the antigen is administered in isolation. Thus, in preferred embodiments, no (significantly) detrimental effect occurs to the further components (in terms of protective efficacy) in the combination as compared to their administration in isolation.

In one aspect of the invention, the immunogenic composition comprising the antigen-adjuvant conjugates is "self-adjuvanting." The term "self adjuvanting" in this context means that administration of the immunogenic composition comprising the antigen-adjuvant conjugate is sufficient to induce an efficacious specific immune response to the antigen, in the absence of other pharmacologically active compounds (e.g. other antigens or adjuvants). For example, in one aspect, a self-adjuvanted composition comprising an antigen conjugated to an adjuvant, provides an improved specific antibody response as measured by serum titres and preferably a clinically significant specific antibody response to the antigen as measured by functional antibody titers and/or cell mediated immunity as measured by T-cell activation.

Examples of disease states in which the immunogenic compositions of the present invention have potentially beneficial effects include allergic diseases, inflammatory conditions, immune-mediated disorders infectious diseases, and cancer. The compounds of the present invention are also of potential use as vaccines comprising antigens conjugated to adjuvants.

As modulators of the immune response, the antigen-adjuvant conjugates of the present invention may be useful, as stand-alone or in combination with other compositions, in the treatment and/or prevention of immune-mediated disorders, including but not limited to inflammatory or allergic diseases such as asthma, allergic rhinitis and rhinoconjunctivitis, food allergy, hypersensitivity lung diseases, eosinophilic pneumonitis, delayed-type hypersensitivity disorders, diabetes, multiple sclerosis, atherosclerosis, pancreatitis, gastritis, colitis, osteoarthritis, psoriasis, sarcoidosis, pulmonary fibrosis, respiratory distress syndrome, bronchiolitis, chronic obstructive pulmonary disease, sinusitis, cystic fibrosis, actinic keratosis, skin dysplasia, chronic urticaria, eczema and all types of dermatitis.

The immunogenic compositions of the present invention may also be useful in the treatment of infectious diseases including, but not limited to, those caused by hepatitis viruses (e.g. hepatitis B virus, hepatitis C virus), human immunodeficiency virus, papillomaviruses, herpesviruses, respiratory viruses (e.g. influenza viruses, respiratory syncytial virus, rhinovirus, metapneumovirus, parainfluenzavirus, SARS), and West Nile virus. The compositions of the present invention may also be useful in the treatment of microbial infections caused by, for example, bacteria, fungi, or protozoa. These include, but are not limited to, tuberculosis, bacterial pneumonia, aspergillosis, histoplasmosis, candidosis, pneumocystosis, leprosy, *chlamydia*, cryptococcal disease, cryptosporidosis, toxoplasmosis, *leishmania*, malaria, ebola and trypanosomiasis.

The immunogenic compositions of the present invention may also be useful in the treatment of various cancers, in particular the treatment of cancers that are known to be responsive to immunotherapy and including, but not limited to, renal cell carcinoma, lung cancer, breast cancer, colorectal cancer, bladder cancer, melanoma, leukaemia, lymphomas and ovarian cancer.

It will be appreciated by those skilled in the art that references herein to treatment or therapy may, depending on the condition, extend to prophylaxis as well as the treatment of established conditions. Thus, antigen-adjuvant conjugates of the present invention may be useful in vaccines and useful as active therapeutic agents.

The immunogenic composition of the present invention, for example, be formulated for oral, topical, inhaled, intranasal, buccal, parenteral (for example intravenous, intradermal, or intramuscular) or rectal administration. In one aspect, the compounds of the present invention are formulated for oral administration. In a further aspect, the compounds the present invention are formulated for topical administration, for example intranasal or inhaled administration.

Formulations

In one embodiment, the immunogenic compositions of the invention are formulated as a vaccine for in vivo administration to the host, such that they confer an antibody titre superior to the criterion for seroprotection for each antigenic component for an acceptable percentage of human subjects. This is an important test in the assessment of a vaccine's efficacy throughout the population. Antigens with an associated antibody titre above which a host is considered to be seroconverted against the antigen are well known, and such titres are published by organisations such as WHO. In one embodiment, more than 80% of a statistically significant sample of subjects is seroconverted, in another embodiment more than 90% of a statistically significant sample of subjects is seroconverted, in a further embodiment more than 93% of a statistically significant sample of subjects is seroconverted and in yet another embodiment 96-100% of a statistically significant sample of subjects is seroconverted.

The amount of antigen in each vaccine dose is selected as an amount which induces an immunoprotective response without significant, adverse side effects in typical vaccines. Such amount will vary depending on which specific antigens are employed. Generally it is expected that each dose will comprise 1-1000 µg of total antigen, or 1-100 µg, or 1-40 µg, or 1-5 µg. An optimal amount for a particular vaccine can be ascertained by studies involving observation of antibody titres and other responses in subjects.

Vaccines of the invention can be packaged in various types of containers e.g. in vials, in syringes, etc. A multidose vial will typically comprise a re-sealable plastic port through which a sterile needle can be inserted to remove a dose of vaccine, which reseals once the needle has been removed.

The vaccine may be supplied in various containers (e.g. 2 or 3). The contents of the containers may be mixed extemporaneously before administering to a host in a single injection or may be administered concomitantly at different sites. The dose of the vaccine, or each vaccine if a kit, is administered concomitantly (in two or more containers) will typically be 0.5 mL.

Administration

The invention provides a method for raising an immune response in a mammal, comprising the step of administering an effective amount of an immunogenic composition of the invention. The compositions can be administered prophylactically (i.e. to prevent infection) as with a vaccine. The immune response is preferably protective and preferably involves antibodies. The method may raise a booster response.

Following an initial administration, subjects may receive one or several booster (subsequent) immunisations adequately spaced. Dosing treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses and between priming and boosting can be routinely determined.

The immunogenic compositions of the present invention may be used to protect or treat a mammal susceptible to infection, by means of administering said composition directly to a patient. Direct delivery may be accomplished by parenteral administration (including but not limited to: intramuscularly, intraperitoneally, intradermally, intravenously, or to the interstitial space of a tissue); or by rectal, oral, vaginal, topical, transdermal, intranasal, ocular, aural, pulmonary or other mucosal administration. In one embodiment, administration is by intramuscular injection to the thigh or the upper arm. Injection may be via a needle (e.g. a hypodermic needle), but needle free injection may alternatively be used. In one embodiment, an intramuscular dose is 0.5 mL.

The terms "comprising", "comprise" and "comprises" herein are intended by the inventors to be optionally substitutable with the terms "consisting of", "consist of" and "consists of", respectively, in every instance. This does not change the normal meaning of these terms, and is only intended to provide basis for the substitution, not to make them equivalent in meaning.

EXAMPLE 1

Oxoadenines Synthesis

Oxoadenines and methods for preparing oxoadenines such as compounds A and C are known in the art and in particular are disclosed in WO2010/018134.

The synthesis of oxoadenine Compound B is carried out according to the scheme 1 and as described below. Compounds 1, 2, 40, 41, 42 and 43 set forth in the synthesis below are additionally described in WO2010/018134 (using the same numbering as in WO2010/018134 patent application).

4-bromopyridine hydrochloride A (2.5 g) was partitioned between 1 N sodium hydroxide (20 ml) and ethyl acetate (3×20 ml). The organic layer was separated, dried over $Na_2SO_4$ and concentrated under vacuum. The resulting oil was dissolved in TEA (2.6 M) and degassed under nitrogen. 4-Pentyn-1-ol (1.1 eq) was added followed by bis(triphenylphosphine)palladium (II) chloride, (0.01 eq) and copper(I) iodide (0.02 eq) and the reaction mixture stirred at reflux for 20 min. Aqueous work-up (ethyl acetate/water) and purification by chromatography on silica gel (gradient 0-30% ethyl acetate in heptane) led to B in 82% yield. B was dissolved in acetic acid (0.05 M) and the solution hydrogenated using an H-Cube® continuous-flow hydrogenation reactor (ThalesNano) (20% $Pd(OH)_2$/C cartridge, 100 bars $H_2$, 90° C., 1 mL/min).

Once the hydrogenation was complete, the reaction mixture was concentrated and dried under vacuum. The resulting crude was dissolved in $CH_2Cl_2$ (0.4 M), and reacted with $Et_3N$ (1.5 eq) and di-t-buty dicarbonate (1.2 eq) at room temperature for 30 min. After aqueous work-up ($CH_2Cl_2$/$H_2O$) and purification by chromatography on silica gel (gradient 0-30% ethyl acetate in heptane) C was isolated in 80% yield: $^1H$ NMR (400 MHz, $CDCl_3$) δ 4.06 (s, 2H), 3.64 (t, 2H), 2.66 (t, 2H), 1.54-1.66 (m, 5H), 1.45 (s, 9H), 1.24-1.39 (m, 8H), 1.08 (m, 2H). CBr$_4$ (1.6 eq) and PPh$_3$ (1.2 eq) were slowly added (exothermic reaction) to a solution of C in CH$_2$Cl$_2$ (0.45 M) at 0° C.

After 5 minutes, the reaction mixture was allowed to warm up to room temperature, stirred at room temperature for 45 min, concentrated and directly purified by chromatography on silica gel (gradient 0-30% ethyl acetate in heptane) to give D in 92% yield. K$_2$CO$_3$ (325 mesh, 3.0 eq) was added to a solution of 43 in DMF (0.25M) and the reaction mixture was sonicated several seconds to obtain a fine suspension then stirred at 60° C. for 1 h. After cooling to 50° C., D (1.2 eq) was added and the reaction mixture stirred overnight at 50° C. After cooling to room temperature and aqueous work-up (ethyl acetate/water) the resulting crude was purified by chromatography on silica gel (gradient 0-10% methanol in chloroform).

The purified product E was dissolved in methanol (0.1 M) and reacted with 4 N HCl in dioxane (6.0 eq) at room temperature for 1 h. The reaction mixture was concentrated and dried under vacuum and the residue purified by chromatography on silica gel (0-100% CHCl$_3$/CH$_3$OH/H$_2$O 90/10/0.5 in CHCl$_3$/CH$_3$OH/H$_2$O 85/15/1.0) to give F in 64% yield (2 steps). $^1$H NMR (400 MHz, CD$_3$OD) gamma 5.14 (m, 1H), 3.81 (t, 2H), 3.36/3.32 (m, 4H), 2.97 (d of t, 2H), 1.92 (m, 2H), 1.75 (p, 2H), 1.72 (m, 1H), 1.57 (m, 2H) 1.5-1.3 (m, 14H), 0.95 (t, 3H); positive ES TOF-MS calc for [M+H]$^+$ 391.28222, found 391.0843.

SCHEME 1

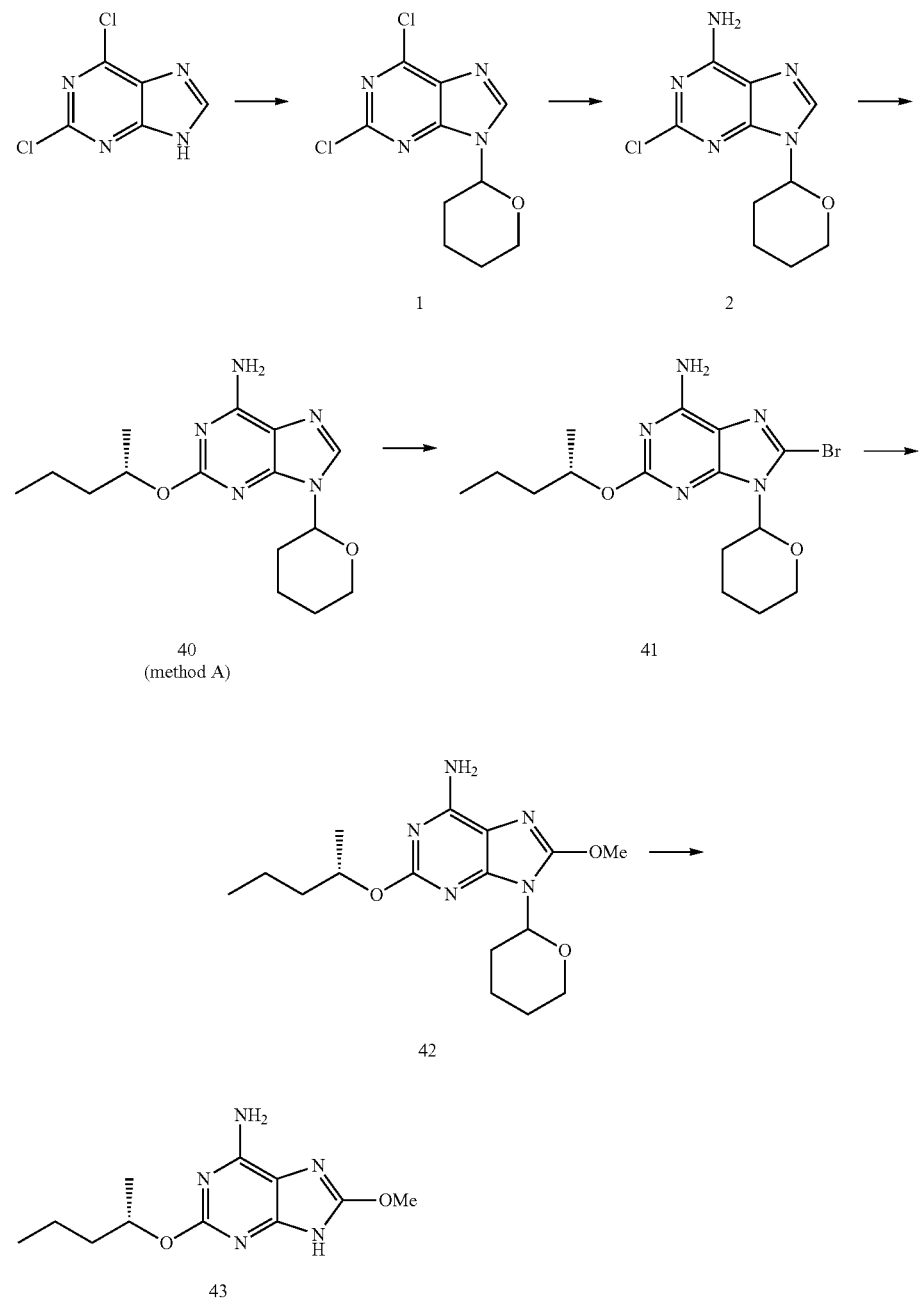

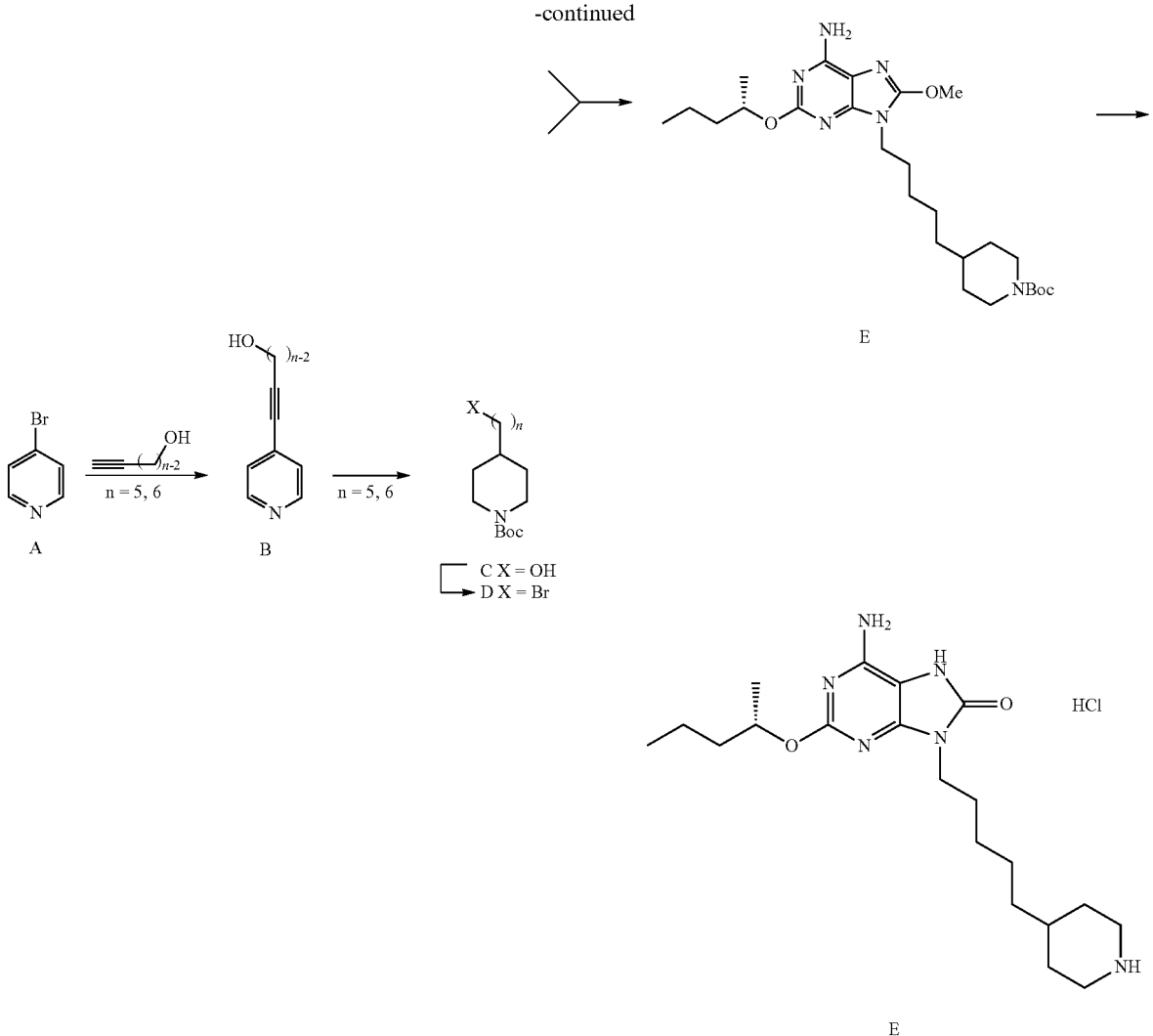

EXAMPLE 2

Example: HBsAg—Compound B Conjugation Process (G-Chemistry)

1) Adjuvant was activated with GMBS by adding 3 equivalents of GMBS and 1.5 equivalents of TEA to 1 equivalent of adjuvant in DMF/H$_2$O 80%/20%. The reaction was incubated at room temperature for 20 minutes.
2) Sample was diluted with acetonitrile and 10 mM ammonium acetate pH=6 and purified by prep RP-HPLC to remove unreacted GMBS and any adjuvant dimer.
3) Factions were collected containing adjuvant activated with GMBS (test by LCMS) and dried by speed vac. Dry adjuvant activated with GMBS was stored at −20° C. until used.
4) Antigen was activated by adding 40 equivalents of 2-iminothiolane (Traut's reagent) to protein solution dropwise while gently mixing solution. The solution was incubated at room temperature for 1.5 hours. The solution was purified by ultrafiltration using 15 ml Amicon ultrafiltration tubes with a 30 kDa MWCO and then washed 7 times with 100 mM phosphate buffer 1) containing 10 mM EDTA and a pH=7.2. (An aliquot of sample was saved for testing by MALDI-TOF.
2) Fifteen equivalents of purified adjuvant activated with GMBS were added to purified antigen activated with Traut's and incubated at room temperature for 2 hours. Copy number was determined by MALDI-TOF.
3) Sample was centrifuged for 5 min and supernatant filtered with 0.1 pm filter to remove any insoluble particles.
4) Filtrate was purified by ultrafiltration using a 15 ml Amicon ultrafiltration tube with a MWCO of 100 kDa. The sample was washed with 100 mM phosphate buffer pH=6.8 with 150 mM NaCl.
5) The purified conjugate was sterile filtered and characterized by RP-HPLC, SEC-HPLC, MALDI-TOF, SDS-PAGE, BCA and LAL.

Example: gE-Compound B conjugation (T-chemistry)

1) Antigen was activated with GMBS by adding 42 equivalents of GMBS dissolved in DMSO to antigen dropwise while gently vortexing and incubating at room temperature for 30 minutes.
2) Unreacted GMBS was purified by ultrafiltration using 15 ml Amicon ultrafiltration tubes with a MWCO of 30 kDa and then washed 5× with 100 mM phosphate buffer, pH=6.8. An aliquot was saved for testing by MALDI-TOF.
3) Adjuvant was activated with Traut's reagent by adding 0.95 equivalents of Traut's reagent and 2.5 equivalents of Hunig's base (N,N-Diisopropylethylamine) in DMF/H$_2$O 90%/10% and then incubated at room temperature for ~1 hour. An aliquot was saved for testing by RP-HPLC.
4) 20 equivalents of adjuvant activated with Traut's was added dropwise to purified antigen activated with GMBS while gently vortexing and incubate at room temperature for 2 hours.
5) The conjugate was purified by ultrafiltration using 15 ml Amicon ultrafiltration tubes with a MWCO of 30 kDa and then washed 8× with 10 mM PB pH=6.8.
6) Remaining unconjugated adjuvant was removed from conjugate by anion exchange. Conjugate was loaded onto a prewashed Pierce strong anion exchange column then washed with 10 mM phosphate buffer pH=6.8 containing increasing concentrations of NaCl (up to 500 mM). Fractions were collected and analyzed by RP-HPLC to determine protein and free adjuvant concentration. Fractions containing conjugate without free adjuvant were combined and desalted by ultrafiltration using a 15 ml Amicon ultrafiltration tube with a 10 kDa MWCO and washed with 10 mM phosphate buffer, pH=6.8
7) Conjugate was sterile filtered and characterize by RP-HPLC, SEC-HPLC, SDS-PAGE, MALDI-TOF, BCA and LAL.

EXAMPLE 3

Analytical Characterization of Conjugates

MALDI-TOF mass spectrometry was used to characterize the mass of the antigen (gB), the antigen conjugated to GMBS and the antigen conjugated to the adjuvant (a TLR2 agonist). The difference in molecular weight between each group was used to calculate the average number of GMBS and adjuvant molecules attached to each antigen. The antigen was protonated with an equal volume of 2% TFA before adding a molar excess of the matrix compound 2,5-Dihydroxy acetophenone. The mixture was then added to a ground steel plate allowing the antigen to co-crystalize in the matrix. The samples were then analysed by MALDI-TOF MS with a Microflex by Bruker. (FIG. 2)

The size of the antigen and antigen/adjuvant conjugates was confirmed by SDS-PAGE along with relative concentration of monomer to higher molecular weight aggregates. A Novex NuPAGE SDS-PAGE Gel System was used with reducing conditions and pre-made gels were chosen based on the size of the antigen. (FIG. 3) In FIG. 3 are shown results for antigen (1), antigen conjugated to a TLR-7/8 agonist (2), antigen conjugated to a TLR-2 agonist (3), antigen activated with GMBS with no adjuvant (4), antigen conjugated to a TLR-7/8 agonist (5), antigen conjugated to both TLR-7/8 and TLR-2 agonists (6). The increase in molecular weight of the conjugates is shown by the shift up of the bands in the gel with respect to the unconjugated antigen. The gel also shows the dimer and trimer are stabilized by the conjugation procedure.

Reverse phase HPLC was used to confirm that all unconjugated adjuvant was removed from the conjugate by the purification process. An HPLC equipped with a PDA detector and a Jupiter C4 column was used with a flow rate of 1 ml/min and a gradient running from 3% acetonitrile and 97% of a trifluoroacetic acid aqueous solution (0.1% trifluoroacetic acid in HPLC water) to 90% acetonitrile and 10% 0.1% trifluoroacetic acid. Absorbance was measured for wavelengths from 215-320 nm. (FIG. 4) The RP-HPLC chromatogram of buffer only (1), antigen only (2) and antigen/adjuvant conjugate (3) shows a small shift in retention time for the conjugate and no unconjugated adjuvant.

Size exclusion chromatography HPLC was also used to confirm the conjugation of the adjuvant to antigen in addition to determining the percentage of monomer of conjugates. An HPLC with a UV detector and a TSK gel (G3000SWXL) column was used with a flow rate of 0.8 ml/min of 10 mM phosphate buffer. Absorbance was measured for wavelengths of 215 and 280 nm. (FIG. 5) The SEC-HPLC chromatogram of buffer only (1), antigen only (2) and antigen/adjuvant conjugate (3) shows a shift in retention time for the conjugate and no unconjugated adjuvant.

A Thermo Scientific Pierce BCA Protein Assay Kit was used to quantify antigen concentration after purification using a BSA protein standard.

A Lonza Kinetic QCL Assay Kit was used to quantify endotoxin levels in purified sterile filtered conjugates.

In cases where the limited solubility of the adjuvant or adjuvant-linker (Traut's) prevents complete purification of unconjugated adjuvant by ultrafiltration it may be necessary to use ion exchange chromatography to remove the remaining adjuvant For example, after the conjugation of Compound B-Traut's to CRM-GMBS and purification by ultrafiltration, approximately 0.9 µg/ml of unconjugated Compound B-Traut's remained in the sample and could not be purified by additional ultrafiltration. To purify by ion exchange, the conjugate was loaded onto a washed anion exchange column where the negatively charge protein associated with the positively charged column. The unconjugated Compound B-Traut's was removed by washing with a 10 mM Phosphate buffer. The purified conjugate was then eluted from the column by washing with 10 mM Phosphate buffer containing increasing concentrations of NaCl. The fractions were collected and examined by RP-HPLC and fractions containing the CRM-Compound B conjugate with no unconjugated Compound B-Traut's were pooled and desalted by ultrafiltration. The final purified Compound B conjugate had less than 0.1 µg/ml of unconjugated Compound B-Traut's.

(FIG. 6). RP-HPLC of fractions collected during ion exchange chromatography of a Compound B conjugate. The column was first washed with 1M NaCl to remove impurities from the column with a retention time of ~3.5 min. The column was washed with 10 mM phosphate buffer prior to being loaded with the conjugate. With the loading and additional washes with 10 mM phosphate buffer the unconjugated Compound B-Traut's with a retention time of ~10.2 min was removed while protein conjugate remained on the column until being eluted with 400 mM NaCl.

EXAMPLE 4

CRM-Compound A conjugates displaying a lower copy number (four Compound A copies) and a higher copy number (six Compound A copies) were then evaluated for their capacity to modulate TLR7 activation (FIG. 7). For this experiment, Compound A was used as a reference and conjugate compounds were diluted so the Compound A copy number was the same at every dilution (same molecular ratio regarding Compound A). Results obtained from this analysis show that conjugate compounds of the present invention are as effective as the ligand alone, Compound A, to activate the TLR7 pathway. This also suggests that conjugate compounds, although they are a lot larger than the ligand itself, do not generate steric hindrance that significantly impacts binding to their receptor.

EXAMPLE 5

Dose-escalation studies identified the optimal dose of conjugates to use in the subsequent experiments. The TLR7/8 oxoadenine (Compound A) was conjugated with the model antigen CRM197 to test for their immunogenic potential in a dose-escalation study.

Method:

Quantification of anti-CRM197 and anti-gB antibodies in mice serum was done using ELISA.

At a terminal time point, whole blood was collected from mice and centrifuged on a vacutainer blood collection tube containing gel for serum separation. Serum samples were stored at −80° C. NUNC Maxisorp plates were first coated with CRM197 or gB protein at 5 or 4 µg/mL, respectively using 50 mM sodium carbonate buffer, overnight at 4° C. ELISA plates were then washed using PBS/0.05% Tween 20. Super Block (ScyTek laboratories) was added to the plates and incubated at 37° C. for at least one hour. The serum samples and standard used herein were pools of pre-quantified mouse antisera against either CRM197 or gB. Standards as well as the sera were plated in each plate and were serially diluted 1:2 in the plates and incubated at 37° C. for 2 hours. After a washing, diluted peroxidase AffiniPure goat anti-mouse IgG, Fcγ fragment specific (Jackson ImmunoResearch Laboratories Inc.) was added for 1 hour at 37° C. A last wash was performed before adding TMB substrate reagent (BD OptEIA™, BD Biosciences) for 30 min at RT. Immediately, plates were stopped using 2N sulfuric acid, and then read at 450 nm using a SpectraMax microplate reader (Molecular Devices, Inc.). Formulations were performed the days of injections. The volume of injection for one mouse was 50 µl. A typical formulation contains: 20 µg-25 µg antigen was diluted with $H_2O$ and PBS pH 7.4 for isotonicity.

Dose-escalation studies were performed to identify the optimal dose of conjugates to use in the subsequent experiments. For reasons related to chemistry and availability of reagent, we started with the TLR7/8 ligand (COMPOUND A) as the adjuvant to conjugate with the model antigen CRM197 to test for their immunogenic potential in a dose-escalation study. Various log 10 doses of CRM-Compound A conjugates from 0.01 to 10 µg (based on total protein content) were evaluated. The results (FIG. 7) showed that 10 µg is an optimal dose to obtain a significant higher humoral response specific to CRM197. This was shown for conjugates having G or T chemistry as explained herein. (FIG. 8)

EXAMPLE 6

Antigen-Adjuvant Conjugate Compared to Admixed Adjuvant

A proof-of-concept study was conducted in BALB/c mice. Mice were injected with various immunogenic compositions (50 µl volume in PBS buffer per mouse using the intramuscular route at day 0-21 and 42 and sera were collected and analysed at day 49 by CRM197 specific ELISA as described in example 5. The following vaccine formulations were tested:

1—CRM alone (CRM197 purified protein) at 10 µg per mouse
2—Conjugate: CRM-Compound A at 10 µg total dose per mouse. The dose of Compound A linked to CRM in this composition is 0.15 µg
3—CRM197 purified protein at 10 µg+0.15 µg of Compound A described as admix of 1×
4—CRM197 purified protein at 10 µg+1.5 µg of Compound A described as admix of 10×
5—CRM197 purified protein at 10 µg+15 µg of Compound A described as admix of 100×

As shown in FIG. 9 CRM-Compound A conjugate is more immunogenic than the simple mixtures of CRM and Compound A, even when the amount of Compound A is 100× higher than what is present in the conjugate. The amount of CRM197 used in the assays was kept constant (10 µg of CRM 197). Only the amount of Compound A molecule was changed in the Ad-Mix formulation. Notably, 0.15 µg of Compound A adjuvant conjugated to 10 µg of CRM197 triggered a significant antibody response directed to CRM 197. This is in contrast to the AdMix, which did not show a significant immunogenic response using 0.15 µg of Compound A. Taken together, these results show that conjugating adjuvant to antigen increases immunogenicity and while employing less adjuvant per dose when compared to admixing of the adjuvant and antigen.

We therefore conducted another proof-of-concept study in BALB/c mice using CRM-Compound B conjugate. Mice were injected with various CRM/Compound B compositions (50 µl volume in PBS buffer per mouse using the intramuscular route at day 0, 21 and 42). Sera were collected and analysed at day 49 by CRM197 specific ELISA as described in Example 5. The following formulations were tested:

1—PBS alone
2—CRM alone (CRM197 purified protein) at 10 µg per mouse
3—Conjugate: CRM-Compound B at 10 µg total dose per mouse. The dose of Compound A linked to CRM in this composition is 0.2 µg
4—CRM197 purified protein at 10 µg+0.2 µg of Compound B described as admix of 1×
5—CRM197 purified protein at 10 µg+2 µg of Compound B described as admix of 10×
6—CRM197 purified protein at 10 µg+20 µg of Compound B described as admix of 100×
7—CRM197 purified protein at 10 µg+TLR4 containing adjuvant (AS01E) previously described herein (2.5 µg of MPL, 2.5 µg QS21 in liposome formulation).

As shown in FIG. 10a CRM-Compound B conjugate is more immunogenic than the simple mixtures of CRM and Compound B (p value less than 0.01), even when the amount of Compound B is 10× higher than what is present in the conjugate. The amount of CRM197 used in the assays was kept constant (10 µg of CRM 197). Only the amount of CRX-Compound B molecule was changed in the Ad-Mix formulation. The results show that the CRM-Compound B conjugate allows for 10-fold decrease of adjuvant to equivalent immunogenicity. Moreover, CRM-Compound B is equivalent to AS01E+CRM for antibody response. The stoichiometric calculation previous to injection shows that 10 µg of CRM protein contains 0.2 µg of Compound B Each CRM containing composition contains an equal amount of CRM antigen (10 ug per mouse). Therefore, for appropriate dose comparison, the 1× of CRM+Compound B admix contains 10 µg of CRM protein and 0.2 µg of Compound B admixed prior to injection in mice. The 10× admix (10 µg of CRM protein and 2 µg of Compound B) and 100× admix (10 µg of CRM protein and 20 µg of Compound B) were also compared. AS01 E, which was used a as a benchmark, (2.5

μg of MPL (TLR4 agonist), 2.5 μg of QS21 in liposome formulation) per injection. We found that CRM-Compound B conjugate exhibits similar CRM-specific antibody response to the CRM+AS01E benchmark, suggesting that TLR7 agonist such as Compound B at very low dose such as 0.2 μg when covalently linked to an antigen could promote a similar antibody response promoted by TLR containing adjuvant benchmark adjuvants such as AS01E. Once again, conjugating adjuvant to antigen shows a beneficial effect on the immune response compared to admixing adjuvant and antigen. Moreover, we show that the CRM-Compound B conjugate triggers a similar IgG CRM197 immune response to the strong TLR4 containing adjuvant called AS01E+CRM197.

T Cell Response in Splenocytes was Measured

Mouse spleens were harvested and single cell suspensions were generated in RPMI+10% FBS using 100 micron cell strainers. Splenocytes were plated in triplicate ($1.5\times10^7$/ml; 200 ul/well) in a 96 well round bottom plate. CRM protein (1 ug/ml), anti-mouse CD28 (1 ug/ml) and anti-mouse CD49d were added to stimulate CRM-specific cells. Unstimulated wells were used as the negative control. BD PMA cocktail (1 ul/well) was used for the positive control. The plate was incubated at 37° overnight followed by a 6 hour incubation with brefeldin A (10 ug/ml). Cells were surface stained with CD3, CD4 & CD8 followed by intracellular staining with TNF and IFNγ using BD Fix/Perm buffer system. Cells were acquired on a LSRII using FACSDiva software. Primary gating was done on CD3+/CD4+ cells for analysis. The data are shown in FIG. 10*b*.

The data show a higher number of CRM-specific CD4 T cells producing IFN-γ in splenocytes from mice immunized with CRM-Compound B conjugate compared to the 1× or 10× admix formulation, suggesting that conjugating Compound B to CRM197 leads to CD4 T cell activation in vivo.

CMI analysis shows that Th1 CMI (CD4-IFNg+ cells) were higher in CRM-Compound B vs CRM alone (FIG. 10*b*). Data could be extracted from the CMI analysis on Th1 CMI (CD4-IFNg+ cells were higher in the conjugate vs CRM alone or Compound A+CRM admix 1× or 10×. Moreover, the CRM-Compound B shows a trend for 3 mice out of 4 to be better for CD4-IFNg+ cells. These data suggest that CRM-Compound B conjugate might trigger T-cell activation and provide better vaccine efficacy, even when using lower amount of adjuvants.

EXAMPLE 7

Three different TLR7/8 compounds conjugated to CRM197 antigen model were tested) for their immunogenicity in mice, two oxoadenines and one imidazoquinoline, Compound C 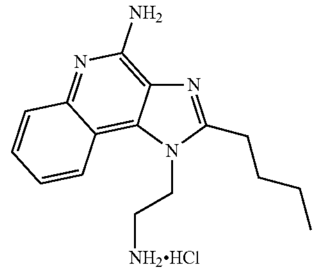 CRM alone (purified CRM197 protein) was included as non-adjuvanted control. Mice (BALB/c CR) were injected with various compositions (50 μl volume in PBS buffer per mouse using the intramuscular route at day 0, 21 and 42. Sera were collected and analysed at day 28 and 49 by CRM197 specific ELISA method as described in example 5. CRM-specific antibody level at 7 days post $2^{nd}$ and post $3^{r}$d injection shows the described CRM-oxoadenine conjugates are potent antigen-adjuvant conjugates, (FIGS. 11 *a* and 11*b*). The CRM-Compound B conjugate exhibits a higher CRM197 specific antibody response among the TLR7/8 agonists tested herein.

EXAMPLE 8

A recombinant antigen (gB from CMV) from an eukaryote expression system in CHO cells was conjugated to an adjuvant and evaluated. BALB/c mice (5 per group) were immunized via the intramuscular route (quadriceps) with either gB or gB-Compound A conjugate (0.001, 0.01, 0.1, 1 or 10 ug diluted in saline) on days 0, 20 and 41. Mice were bled for serum collection on days 31 (post 2) and 52 (post 3). Data are shown in FIG. 12 *a*.

Mouse spleens were harvested and single cell suspensions were generated in RPMI+10% FBS using 100 micron cell strainers. Splenocytes were plated in triplicate ($1.5\times10^7$/ml; 200 ul/well) in a 96 well round bottom plate. gB (4 ug/ml), anti-mouse CD28 (1 ug/ml) and anti-mouse CD49d were added to stimulate gB-specific cells. Unstimulated wells were used as the negative control. BD PMA cocktail (1 ul/well) was used for the positive control. The plate was incubated at 37° overnight followed by a 6 hour incubation with brefeldin A (10 ug/ml). Cells were surface stained with CD3, CD4 & CD8 followed by intracellular staining with IL-2, IL-4, TNF and IFNγ using BD Fix/Perm buffer system. Cells were acquired on a LSRII using FACS Diva software. Primary gating was done on CD3+/CD4+cells for analysis. The data are shown in FIG. 12*b*.

The immunogenicity data show that gB-Compound A conjugate used at 0.01 μg dose promote a one hundred fold (2×Log 10) higher gB specific antibody response compared to gB alone non-adjuvanted. Interestingly, benefit of the gB-Compound A conjugate over gB alone was not clearly demonstrated in higher doses, Despite the IgG data not being dose-dependent, data from the cell mediated immunity (CMI) analysis suggest that Th1 CMI (CD4-IFNg+ cells were higher in gB-Compound A vs gB alone (FIG. 12*b*). Th1 CMI (CD4+IFNg+gB specific T cells were higher in gB-Compound A vs gB alone. Taken together, the antibody and T cell activation data suggest us that low amounts of gB-Compound A conjugate trigger T-cell activation and potentially provide a functional neutralizing antibody response to herpesvirus antigen such as gB from hCMV.

EXAMPLE 9

A vaccine dose-escalation study in pigs (Yorkshire-Duroc-Landrace mix background) was performed to identify the appropriate dose for subsequent studies in large animals. The two types of chiral chemistry described above conjugation G and T and three vaccine concentrations were tested (1, 10 and 100 μg).

Pigs were immunized with 1 ml of vaccine at day 0 and 21 and sera collected at day 31 (10 days post secondary injection). ELISA were performed as described in Example 5 except that the secondary antibody conjugated to HRP was a goat anti pig IgG (Bethyl Laboratories). As described in FIG. 13, CRM-Compound A triggers a CRM197 specific IgG response close to a dose-escalation manner. All the animals (5/5) receiving the 100 µg dose of CRM (=1.5 ug of Compound A) responded to the CRM-Compound A. Therefore, the 100 µg dose of CRM was chosen for the further studies in farm pigs.

A brief adverse effect visual assessment on injection site was performed on 2 random chosen pigs by testing an extra dose of 150 µg of Compound A alone. No visual adverse effect of the injected site was observed, suggesting that Compound A molecules have a good safety profile.

EXAMPLE 10

To better identify the most promising TLR conjugate for CRM197 using the 100 µg dose, three TLR7/8 adjuvant-antigen conjugates were prepared: CRM-Compound A; CRM-Compound C; and CRM-Compound B. In addition, a TLR2 adjuvant-antigen conjugate was tested. (data not shown). A non-adjuvanted CRM197 alone was used as the control. Yorkshire-Landrace farm pigs were immunized at day 0, 21 and 42 and final sera collected at day 52. The pig specific ELISA was performed as described in Example 5. Results demonstrating anti CRM IgG response in final bleed are shown in FIG. 14.

The anti CRM197 IgG response in CRM-Compound B suggests that Compound B is active and immunogenic in farm pigs.

EXAMPLE 11

Intradermal Immunization of Swine

We evaluated the intradermal route of immunization using the CRM-Compound B conjugate. 4 months old Yorkshire-Landrace-Cambrio pigs were immunized in the flanc derma at day 0 and 23 with 100 µl various vaccines. Sera were collected at day 37 and CRM197 IgG specific ELISA was performed as previously described in example 5. The animal groups were the following:

| Groups | Vaccine | Antigen dose (µg) | No. of animals/group |
|---|---|---|---|
| 1 | CRM | 10 µg | 3 |
| 2 | CRM-Compound B | 10 µg | 4 |
| 3 | CRM | 100 µg | 3 |
| 4 | CRM-Compound B | 100 µg | 4 |

The IgG anti CRM197 specific measurement shows that CRM-Compound B conjugate at 100 µg is significantly immunogenic compared to non-adjuvanted antigen alone control using the intradermal route. These antibody titers between the range of 10 000 and 110 000 ng/ml from the CRM-Compound B conjugate suggest that the intradermal route of immunization is also appropriate for TLR7/8-antigen conjugates vaccination. (FIG. 15)

EXAMPLE 12

Quantification of anti-HBs antigen in Yorkshire-Landrace farm pigs in serum was done using ELISA. Farm pigs were immunized at day 1, day 28 and serum were collected at day 58 (terminal time point). Whole blood was collected and centrifuged on a vacutainer blood collection tube containing gel for serum separation. Serum samples were stored at −80° C. Maxisorp 96-well flat-bottom plates (Nunc cat: 439454) were coated with 100 µl per well of Hepatitis B Surface Antigen diluted at 2 µg/ml in carbonate-bicarbonate coating buffer at 50 mM pH9.6. For standard curves, 100 µl per well of Goat anti-pig IgG capture antibody (Bethyl cat: A100-104A) diluted 1/100 in carbonate-bicarbonate coating buffer were dispensed. Plates were incubated for 1 hour at room temperature. Plates were washed (4×250 µl) using wash buffer (TBS containing 0.05% Tween-20) and then, blocked with 200 µl per well of blocking solution (TBS containing 0.05% of Tween-20 and 1% of BSA (Sigma cat: A7030)). Plates were then incubated for 30 minutes at room temperature.

Blocking solution was discarded and 100 µl per well of Blocking solution was dispensed into plates. In the first row of the plates, 100 µl of pig reference serum (Bethyl cat: RS10-107) diluted 1/6600 or samples (previously pre-diluted if needed) were added followed by a two-fold serial dilution for a final volume into each well of 100 µl. Plates were incubated for 1 hour at room temperature. Plates were washed and 100 µl per well of anti-pig IgG HRP-conjugated (Bethyl cat: A100-104P) diluted 1/75000 in blocking solution were dispensed. Plates were incubated 30 minutes at room temperature. Plates were washed and 100 µl per well of TMB substrate (BD cat: 555214) were added into plates for 30 minutes at room temperature protected from light. The reaction was stopped using 100 µl per well of stop solution ($H_2SO_4$ 1M). The plate reading was performed immediately on a microplate reader at 450 nm using a SpectraMax microplate reader (Molecular Devices, Inc.). Results were analyzed with a Soft Max Pro template following this criteria: % CV below 30% between a minimum of 2 calculated concentrations for final quantification.

Figure 16:
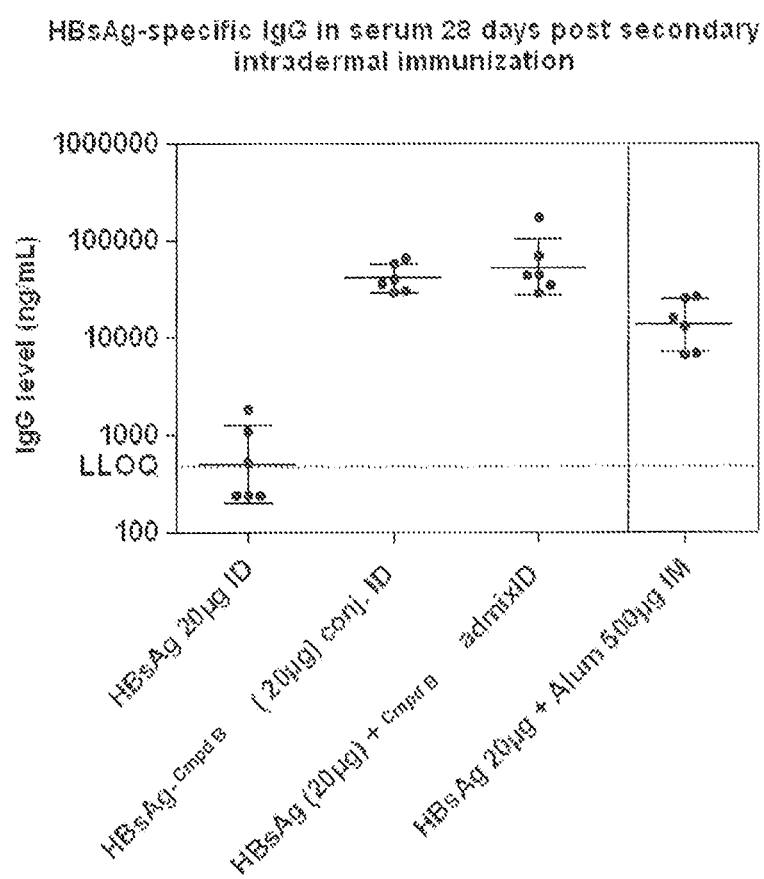
FIG. 16 Evaluation of the immunogenicity of HBs Ag conjugated to Compound B vs admix using the intradermal route of immunization in Yorkshire-Landrace Duroc farm pig intradermal model. Comparison is also made with the intramuscular route (HBsAg+Alum).

Antibody response (FIG. 16) result shows that the vaccine HBsAg-Compound B conjugate using the intradermal route is significantly higher than the standard intramuscular vaccine HBsAg-Alum (t unpaired test P=0.0034). These results suggest that TLR7 conjugated vaccines are highly immunogenic compared to standard intramuscular vaccines formulations such as with Alum.

The invention claimed is:

1. An immunogenic composition comprising an antigen-adjuvant conjugate, said conjugate comprises an oxoadenine compound covalently linked to an antigen, wherein the oxoadenine compound has a structure selected from the group of

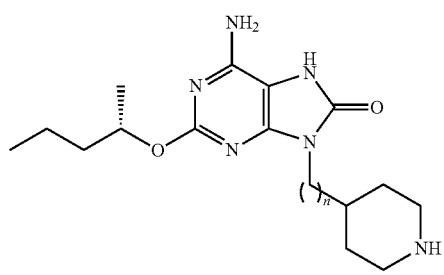

9 n = 1 CRX-692
10 n = 5 CRX-725

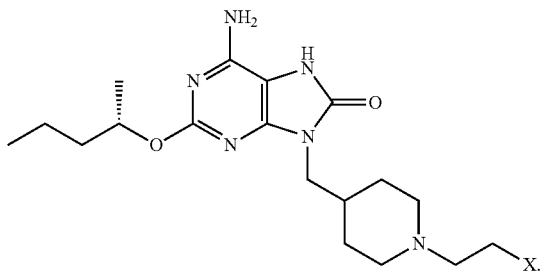

11 X = OH (CRX-748)
12 X = NH₂ (CRX-753)

2. The immunogenic composition according to claim 1 wherein 2, 3, 4, 5, 6, 7, 8, 9 or 10 molecules of the oxoadenine compound are covalently linked to each antigen molecule.

3. The immunogenic composition of claim 1 wherein the oxoadenine compound is

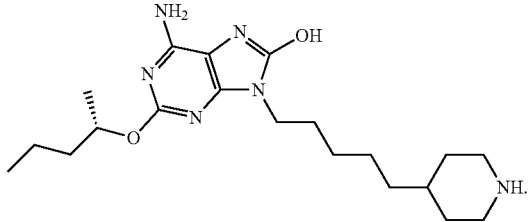 [SMILES: CCC[C@H](C)Oc1nc(N)c2nc(O)n(CCCCCC3CCNCC3)c2n1]

4. The immunogenic composition of claim 1 wherein the oxoadenine compound is linked to the antigen via a crosslinking agent and wherein the crosslinking agent is a hydrophilic compound.

5. The immunogenic composition of claim/wherein the crosslinking agent increases the aqueous solubility of the oxoadenine compound compared to the solubility in the absence of the crosslinking agent.

6. The immunogenic composition of claim 1 wherein the oxoadenine compound is linked to the antigen via a crosslinking agent and wherein the crosslinking agent is a charged compound.

7. The immunogenic composition of claim 6 wherein the crosslinking agent is Traut's reagent reacted with GMBS.

8. The immunogenic composition of claim 1 wherein the oxoadenine compound is linked to the antigen via a crosslinking agent and wherein the crosslinking agent is a Hetero-Bifunctional Crosslinker.

9. The immunogenic composition of claim 1 further comprising a carrier protein wherein antigen is bound to the carrier and the oxadenine compound is linked to the carrier protein.

10. The immunogenic composition of claim 1 wherein the antigen is an antigen selected from the group consisting of: CRM-197, Tetanus Toxoid, HA, gB of CMV virus, preF, Hash-2, HPV E7, Pertussis toxin (PT), HBs, Ovalbumin, HIV, PRAME and MAGE antigen.

11. The immunogenic composition of claim 10, wherein the HBs antigen is S antigen.

12. The immunogenic composition of claim 10, wherein the HIV antigen is gag or env.

13. The immunogenic composition of claim 10, wherein the MAGE antigen is MAGE A3.

14. The immunogenic composition of claim 1 wherein the oxoadenine compound is

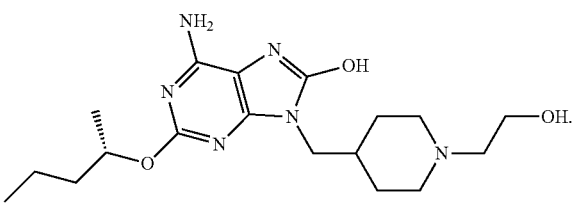

16. The immunogenic composition of claim 1 wherein the oxoadenine compound is

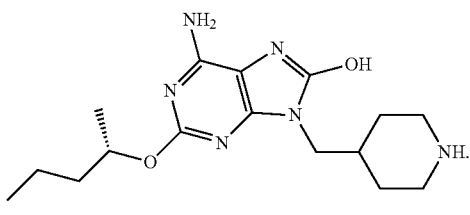 [SMILES: CCC[C@H](C)Oc1nc(N)c2nc(O)n(CC3CCNCC3)c2n1]

15. The immunogenic composition of claim 1 wherein the oxoadenine compound is

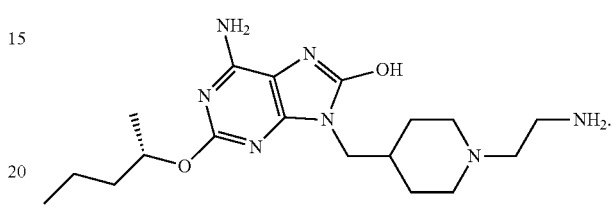

* * * * *